United States Patent [19]
Balasubramaniam

[11] Patent Number: 5,604,203
[45] Date of Patent: Feb. 18, 1997

[54] ANALOGS OF PEPTIDE YY AND USES THEREOF

[75] Inventor: Ambikaipakan Balasubramaniam, Cincinnati, Ohio

[73] Assignee: University of Cincinnati, Cincinnati, Ohio

[21] Appl. No.: 329,151

[22] Filed: Oct. 24, 1994

Related U.S. Application Data

[63] Continuation-in-part of Ser. No. 109,326, Aug. 19, 1993, abandoned, which is a continuation-in-part of Ser. No. 38,534, Mar. 29, 1993, abandoned.
[51] Int. Cl.$^6$ .............................. A61K 38/00; C07K 5/00; C07K 7/00; C07K 17/00
[52] U.S. Cl. .................... 514/12; 514/13; 514/14; 514/15; 514/16; 514/17; 530/324; 530/325; 530/326; 530/327; 530/328; 530/329
[58] Field of Search ................ 514/12–17; 530/324–329

[56] References Cited

U.S. PATENT DOCUMENTS 5,026,685  6/1991  Boublik et al. ........................ 514/13

FOREIGN PATENT DOCUMENTS 64-6294  10/1989  Japan .

OTHER PUBLICATIONS

Balasubramaniam et al., "Structure–Activity Studies of Peptides YY(22–36): N-α-Ac-[Phe$^{27}$]PYY(22–36), a Potent Antisecretory Peptide in Rat Jejunum;" Peptides 14:1011–1016, 1993.
Balasubramaniam et al., "Syntheses and Receptor Affinities of Partial Sequences of Peptide YY (PYY);" Peptide Research 1:32–35, 1988.
Feinstein et al., "Structural Requirements for Neuropeptide Y$^{18-36}$–Evoked Hypotension: A Systematic Study;" J. Med. Chem. 35:2836–2843, 1992.
Ishiguro et al., "Synthesis of Peptide Fragments of Neuropeptide Y: Potent Inhibitors of Calmodulin–Stimulated Phosphodiesterase;" Chem. Pharm. Bull. 36:2720–2723, 1988.
Lundberg et al., "Localization of Peptide YY (PYY) in Gastrointestinal Endocrine Cells and Effects on Intestinal Blood Flow and Motility;" Proc. Natl. Acad. Sci. USA 79:4471–4475, 1982.
Servin et al., "Peptides–YY and Neuropeptide–Y Inhibit Vasoactive Intestinal Peptide–Stimulated Adenosine 3', 5'–Monophosphate Production in Rat Small Intestine: . . . ;"Endocrinology 124:692–700, 1989.
Tatemoto "Isolation and Characterization of Peptide YY (PYY), a Candidate Gut Hormone that Inhibits Pancreatic Exocrine Secretion;" Proc. Natl. Acad. Sci. USA 79:2514–2518, 1982.
Voisin et al., "Characterization, Signal Transduction, and Expression during Cell Differentiation;" New York Academy of Sciences 611:343–346, 1990.
Balasubramaniam et al., "Synthesis, Receptor Affinities and Antisecretory Effects of Peptide YY (22–36) Analogs", presented at the Twelfth American Peptide Symposium, Jun. 16–21, 1991 in Cambridge, Massachusetts.

Primary Examiner—Toni R. Scheiner
Assistant Examiner—Sheela J. Huff
Attorney, Agent, or Firm—Fish & Richardson P.C.; William E. McGowan

[57] ABSTRACT

The invention provides analogs of PYY. The invention also provides compositions and methods useful for controlling biological activities such as cell proliferation, nutrient transport, lipolysis, and intestinal water and electrolyte secretion.

29 Claims, 5 Drawing Sheets

ANALOGS OF PEPTIDE YY AND USES THEREOF

STATEMENT AS TO FEDERALLY SPONSORED RESEARCH

This invention was made in part with Government funding and the Government therefore has certain rights in the invention.

This application is a continuation-in-part of Ser. No. 08/109,326 filed on Aug. 19, 1993 now abandoned, which is a continuation-in-part of Ser. No. 08/038,534 filed on Mar. 29, 1993, now abandoned.

BACKGROUND OF THE INVENTION

This invention relates to peptide derivatives which are useful as therapeutic agents in the treatment of gastroenterological disorders.

Peptide YY (PYY) is a 36-residue peptide amide isolated originally from porcine intestine, and localized in the endocrine cells of the gastrointestinal tract and pancreas (Tatemoto et al. *Proc. Natl. Acad. Sci.* 79:2514, 1982). Peptide YY has N-terminal and C-terminal tyrosine amides; accordingly, these two tyrosines give PYY its name (Y represents the amino acid tyrosine in the peptide nomenclature). In addition PYY shares a number of central and peripheral regulatory roles with its homologous peptide neuropeptide Y (NPY), which was originally isolated from porcine brain (Tatemoto, *Proc. Natl. Acad. Sci.* 79:5485, 1982). In contrast with the cellular location of PYY, NPY is present in submucous and myenteric neurons which innervate the mucosal and smooth muscle layers, respectively (Ekblad et al. *Neuroscience* 20:169, 1987). Both PYY and NPY are believed to inhibit gut motility and blood flow (Laburthe, *Trends Endocrinol. Metab.* 1:168, 1990), and they are also thought to attenuate basal (Cox et al. *Br. J. Pharmacol.* 101:247, 1990; Cox et al. *J. Physiol.* 398:65, 1988; Cox et al. *Peptides* 12:323, 1991; Friel et al. *Br. J. Pharmacol.* 88:425, 1986) and secretagogue-induced intestinal secretion in rats (Lundberg et al. *Proc. Natl. Acad. Sci USA* 79:4471, 1982; Playford et al. *Lancet* 335:1555, 1990) and humans (Playford et al. supra), as well as stimulate net absorption (MacFadyen et al. *Neuropeptides* 7:219, 1986). Furthermore, plasma PYY levels have been reported to be elevated in several diseases that cause diarrhea (Adrian et al. *Gastroenterology* 89:1070, 1985). Taken together, these observations suggest that PYY and NPY are released into the circulation after a meal (Adrian et al. *Gastroenterology* 89:1070, 1985; Balasubramaniam et al. *Neuropeptides* 14:209, 1989), and thus may play a physiological role in regulating intestinal secretion and absorption, serving as natural inhibitors of diarrhea.

A high affinity PYY receptor system which exhibits a slightly higher affinity for PYY than NPY has been characterized in rat intestinal epithelia (Laburthe et al. *Endocrinology* 118:1910, 1986; Laburthe, *Trends Endocrinol. Metab.* supra) and shown to be negatively coupled to adenylate cyclase (Servin et al. *Endocrinology* 124:692, 1989). Consistently, PYY exhibited greater antisecretory potency than NPY in voltage clamped preparations of rat small intestine (Cox et al. *J. Physiol.* supra), while C-terminal fragments of NPY were found to be less effective in their antisecretory potency than PYY (Cox et al. *Br. J. Pharmacol.* supra). Structure-activity studies using several partial sequences have led to the identification of PYY(22–36) as the active site for interacting with intestinal PYY receptors (Balsubramaniam et al. *Pept. Res.* 1:32, 1988).

In addition, PYY has been implicated in a number of physiological activities including nutrient uptake (see, e.g., Bilcheik et al. *Digestive Disease Week* 506:623, 1993), cell proliferation (see, e.g., Laburthe, *Trends Endocrinol. Metab.* 1:168, 1990; Voisin et al. *J. Biol. Chem,* 1993), lipolysis (see, e.g., Valet et al., *J. Clin. Invest.* 291, 1990), and vasoconstriction (see, e.g., Lundberg et al., *Proc. Natl. Acad. Sci., USA* 79: 4471, 1982).

The amino acid sequences of porcine and human PYY are as follows:

porcine PYY YPAKPEAPGEDASPEELSRYYASL-RHYLNLVTRQRY (SEQ. ID. NO. 1)

human PYY YPIKPEAPGEDASPEELNRYYASL-RHYLNLVTRQRY (SEQ. ID. NO. 2)

The amino acid sequence for dog PYY and rat is the same as porcine PYY.

SUMMARY OF THE INVENTION

In one aspect, the present invention features novel analogs of peptide YY of the formula:

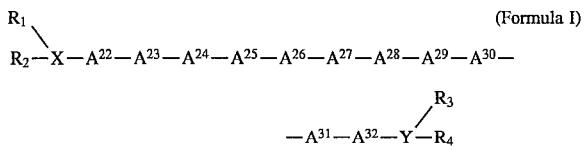

wherein

X is a chain of 0–5 amino acids, inclusive, the N-terminal one of which is bonded to $R_1$ and $R_2$;

Y is a chain of 0–4 amino acids, inclusive, the C-terminal one of which is bonded to $R_3$ and $R_4$;

$R_1$ is H, $C_1$–$C_{12}$ alkyl (e.g., methyl), $C_6$–$C_{18}$ aryl (e.g., phenyl, naphthaleneacetyl), $C_1$–$C_{12}$ acyl (e.g., formyl, acetyl, and myristoyl), $C_7$–$C_{18}$ aralkyl (e.g., benzyl), or $C_7$–$C_{18}$ alkaryl (e.g., p-methylphenyl);

$R_2$ is H, $C_1$–$C_{12}$ alkyl (e.g., methyl), $C_6$–$C_{18}$ aryl (e.g., phenyl, naphthaleneacetyl), $C_1$–$C_{12}$ acyl (e.g., formyl, acetyl, and myristoyl), $C_7$–$C_{18}$ aralkyl (e.g., benzyl), or $C_7$–$C_{18}$ alkaryl (e.g., p-methylphenyl);

$A^{22}$ is an aromatic amino acid, Ala, Aib, Anb, N-Me-Ala, or is deleted;

$A^{23}$ is Ser, Thr, Ala, Aib, N-Me-Ser, N-Me-Thr, N Me-Ala, or is deleted;

$A^{24}$ is Leu, Ile, Val, Trp, Gly, Nle, Nva, Aib, Anb, N-Me-Leu, or is deleted;

$A^{25}$ is Arg, Lys, homo-Arg, diethyl-homo-Arg, Lys-ε-NH—R (where R is H, a branched or straight chain $C_1$–$C_{10}$ alkyl group, or an aryl group), Orn, or is deleted;

$A^{26}$ is Ala, His, Thr, 3-Me-His, 1-Me-His, β-pyrozolylalanine, N-Me-His, Arg, Lys, homo-Arg, diethyl-homo-Arg, Lys-ε-NH—R (where R is H, a branched or straight chain $C_1$–$C_{10}$ alkyl groups or an aryl group), Orn, or is deleted;

$A^{27}$ is an aromatic amino acid other than Tyr;

$A^{28}$ is Leu, Ile, Val, Trp, Nle, Nva, Aib, Anb, or N-Me-Leu;

$A^{29}$ is Asn, Ala, Gln, Gly, Trp, or N-Me-Asn;

$A^{30}$ is Leu, Ile, Val, Trp, Nle, Nva, Aib, Anb, or N-Me-Leu;

$A^{31}$ is Val, Leu, Ile, Trp, Nle, Nva, Aib, Anb, or N-Me-Val;

$A^{32}$ is Thr, Ser, N-Me-Ser, N-Me-Thr, or D-Trp;

$R_3$ is H, $C_1$–$C_{12}$ alkyl (e.g., methyl), $C_6$–$C_{18}$ aryl (e.g., phenyl, naphthaleneacetyl), $C_1$–$C_{12}$ acyl (e.g., formyl, acetyl, and myristoyl), $C_7$–$C_{18}$ aralkyl (e.g., benzyl), or $C_7$–$C_{18}$ alkaryl (e.g., p-methylphenyl); and $R_4$ is H, $C_1$–$C_{12}$ alkyl (e.g., methyl), $C_6$–$C_{18}$ aryl (e.g., phenyl, naphthaleneacetyl), $C_1$–$C_{12}$ acyl (e.g., formyl, acetyl, and myristoyl), $C_7$–$C_{18}$ aralkyl (e.g., benzyl), or $C_7$–$C_{18}$ alkaryl (e.g., p-methylphenyl), or a pharmaceutically acceptable salt thereof.

In preferred embodiments, $A^{27}$ is Phe, Nal, Bip, Pcp, Tic, Trp, Bth, Thi, or Dip.

In preferred embodiments X is $A^{17}$-$A^{18}$-$A^{19}$-$A^{20}$-$A^{21}$ wherein $A^{17}$ is Cys, Leu, Ile, Val, Nle, Nva, Aib, Anb, or N-Me-Leu;

$A^{18}$ is Cys, Ser, Thr, N-Me-Ser, or N-Me-Thr;

$A^{19}$ is Arg, Lys, homo-Arg, diethyl-homo-Arg, Lys-ε-NH—R (where R is H, a branched or straight chain $C_1$–$C_{10}$ alkyl group, or $C_6$–$C_{18}$ aryl group), Cys, or Orn;

$A^{20}$ is an aromatic amino acid, or Cys; and $A^{21}$ is an aromatic amino acid, Cys, or a pharmaceutically acceptable salt thereof. In yet other preferred embodiments, Y is $A^{33}$-$A^{34}$-$A^{35}$-$A^{36}$ wherein $A^{33}$ is Arg, Lys, homo-Arg, diethyl-homo-Arg, Lys-ε-NH—R (where R is H, a branched or straight chain $C_1$–$C_{10}$ alkyl group, or an aryl group), Cys, or Orn;

$A^{34}$ is Cys, Gln, Asn, Ala, Gly, N-Me-Gln, Aib, or Anb;

$A^{35}$ is Arg, Lys, homo-Arg, diethyl-homo-Arg, Lys-ε-NH—R (where R is H, a branched or straight chain $C_1$–$C_{10}$ alkyl group, or an aryl group), Cys, or Orn; and $A^{36}$ is an aromatic amino acid, Cys or a pharmaceutically acceptable salt thereof.

Preferably, the compound has the formula: N-α-Ac-Ala-Ser-Leu-Arg-His-Phe-Leu-Asn-Leu-Val-Thr-Arg-Gln-Arg-Tyr-NH$_2$ (SEQ. ID. NO. 3), H-Ala-Ser-Leu-Arg-His-Phe-Leu-Asn-Leu-Val-Thr-Arg-Gln-Arg-Tyr-NH$_2$ (SEQ. ID. NO. 4), N-α-Ac-Ala-Ser-Leu-Arg-His-Trp-Leu-Asn-Leu-Val-Thr-Arg-Gln-Arg-Tyr-NH$_2$ (SEQ. ID. NO. 5), N-α-Ac-Ala-Ser-Leu-Arg-His-Thi-Leu-Asn-Leu-Val-Thr-Arg-Gln-Arg-Tyr-NH$_2$ (SEQ. ID. NO. 6), N-α-Ac-Tyr-Ser-Leu-Arg-His-Phe-Leu-Asn-Leu-Val-Thr-Arg-Gln-Arg-Tyr-NH$_2$ (SEQ. ID. NO. 7) or a pharmaceutically acceptable salt thereof.

In another aspect the invention features novel analogs of peptide YY of the formula:

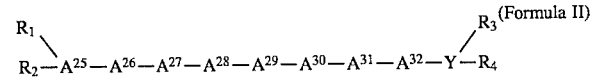

wherein the N-terminal amino acid is bonded to $R_1$ and $R_2$; Y is a chain of 0–4 amino acids, inclusive the C-terminal one of which is bonded to $R_3$ and $R_4$;

$R_1$ is H, $C_1$–$C_{12}$ alkyl (e.g., methyl), $C_6$–$C_{18}$ aryl (e.g., phenyl, napthaleneacetyl), $C_1$–$C_{12}$ acyl (e.g., formyl, acetyl, and myristoyl), $C_7$–$C_{18}$ aralkyl (e.g., benzyl), or $C_7$–$C_{18}$ alkaryl (e.g., p-methylphenyl);

$R_2$ is H, $C_1$–$C_{12}$ alkyl (e.g., methyl), $C_6$–$C_{18}$ aryl (e.g., phenyl, napthaleneacetyl), $C_1$–$C_{12}$ acyl (e.g., formyl, acetyl, and myristoyl), $C_7$–$C_{18}$ aralkyl (e.g., benzyl), or $C_7$–$C_{18}$ alkaryl (e.g., p-methylphenyl);

$A^{25}$ is Arg, Lys, homo-Arg, diethyl-homo-Arg, Lys-ε-NH—R (where R is H, a branched or straight chain $C_1$–$C_{10}$ alkyl group, or an aryl group), Orn, or is deleted;

$A^{26}$ is Ala, His, Thr, 3-Me-His, 1-Me-His, β-pyrozolylalanine, N-Me-His, Arg, Lys, homo-Arg, diethyl-homo-Arg, Lys-ε-NH-R (where R is H, a branched or straight chain $C_1$–$C_{10}$ alkyl group, or an aryl group), Orn, or is deleted;

$A^{27}$ is an aromatic amino acid;

$A^{28}$ is Leu, Ile, Val, Trp, Nle, Nva, Aib, Anb, or N-Me-Leu;

$A^{29}$ is Asn, Ala, Gln, Gly, Trp, or N-Me-Asn;

$A^{30}$ is Leu, Ile, Val, Trp, Nle, Nva, Aib, Anb, or N-Me-Leu;

$A^{31}$ is Val, Ile, Trp, Nva, Aib, Anb, or N-Me-Val;

$A^{32}$ is Thr, Ser, N-Me-Ser, N-Me-Thr, or D-Trp;

$R_3$ is H, $C_1$–$C_{12}$ alkyl (e.g., methyl), $C_6$–$C_{18}$ aryl (e.g., phenyl, napthaleneacetYl), $C_1$–$C_{12}$ acyl (e.g., formyl, acetyl, and myristoyl), $C_7$–$C_{18}$ aralkyl (e.g., benzyl), or $C_7$–$C_{18}$ alkaryl (e.g., p-methylphenyl); and $R_4$ is H, $C_1$–$C_{12}$ alkyl (e.g., methyl), $C_6$–$C_{18}$ aryl (e.g., phenyl, napthaleneacetyl), $C_1$–$C_{12}$ acyl (e.g., formyl, acetyl, and myristoyl), $C_7$–C18 aralkyl (e.g., benzyl), or $C_7$–$C_{18}$ alkaryl (e.g., p-methylphenyl), or a pharmaceutically acceptable salt thereof.

In preferred embodiments $A^{27}$ is Phe, Nal, Bip, Pcp, Tic, Trp, Bth, Thi, or Dip.

In preferred embodiments Y is $A^{33}$-$A^{34}$-$A^{35}$-$A^{36}$ wherein $A^{33}$ is Arg, Lys, homo-Arg, diethyl-homo-Arg, Lys-ε-NH—R (where R is H, a branched or straight chain $C_1$–$C_{10}$ alkyl group, or $C_6$–$C_{18}$ aryl group), Cys, or Orn;

$A^{34}$ is Gln, Asn, Ala, Gly, N-Me-Gln, Aib, Cys, or Anb;

$A^{35}$ is Arg, Lys, homo-Arg, diethyl-homo-Arg, Lys-ε-NH—R (where R is H, a branched or straight chain $C_1$–$C_{10}$ alkyl group, or $C_6$–$C_{18}$ aryl group), Cys, or Orn; and $A^{36}$ is an aromatic amino acid, Cys, or a pharmaceutically acceptable salt thereof.

Preferably, the compound has the formula N-α-Ac-Arg-His-Phe-Leu-Asn-Leu-Val-Thr-Arg-Gln-Arg-Tyr-NH$_2$ (SEQ. ID. NO. 8).

In another aspect, the invention features novel dimeric analogs of peptide YY. The dimer may be formed by either including two peptides of Formula I, two peptides of Formula II, or one peptide of Formula I and one peptide of Formula II. In one embodiment, the dimer is formed by utilizing a dicarboxylic acid linker capable of binding to a free amine, either primary or secondary, located within each peptide. See, e.g., R. Vavrek and J. Stewart, *Peptides: Structure and Function* 381–384 (Pierce Chemical Co. 1983). Examples of suitable dicarboxylic acid linkers are succinic acid, glutamic acid, and phthalic acid. In other embodiments, the dimer is formed by utilizing an amino acid linker capable of binding to a free amine group of one peptide and a free carboxyl group of the other peptide. Preferably, the amino acid linker is a non α-amino acid. Examples of suitable amino acid linkers are amino-caproic acid and amino-valeric acid. In yet another embodiment, the dimer is formed by a disulfide bridge between cysteines located within each peptide. See, e.g., M. Berngtowicz and G. Piatsueda, *Peptides: Structure and Function* 233–244 (Pierce Chemical Co. 1985); F. Albericio, et al., Peptides 1990. 535 (ESCOM 1991).

In yet another aspect, the invention features analogs of Formula I or Formula II having at least one pseudopeptide bond between amino acid residues. By "pseudopeptide bond" is meant that the carbon atom participating in the bond between two residues is reduced from a carbonyl carbon to a methylene carbon, i.e., $CH_2$—NH; or less preferably that of CO—NH is replaced with any of $CH_2$—S, $CH_2$—$CH_2$, $CH_2$—O, or $CH_2$—CO. A pseudopeptide peptide bond is symbolized herein by "Ψ". Preferably, the pseudopeptide bonds are located between one or more amino acid residues, e.g., $A^{28}\Psi A^{29}$, $A^{29}\Psi A^{30}$, $A^{30}\Psi A^{31}$, $A^{31}\Psi A^{32}$, $A^{32}\Psi A^{33}$, $A^{33}\Psi A^{34}$, $A^{34}\Psi A^{35}$, or $A^{35}\Psi A^{36}$. In addition, such pseudopeptide bond analogs can be used to form dimeric analogs as is described above. A detailed discussion of the chemistry of pseudopeptide bonds is given in Coy et al. (1988) *Tetrahedron* 44:835–841.

In yet another aspect, the invention features radiolabeled analogs of Formula I and Formula II. Preferably, the analogs have a tyrosine iodinated on the phenyl ring at carbon position 3 or 5. The radioactive iodine is preferably $I^{125}$ or $I^{123}$. An example of the chemistry associated with iodinated tyrosine residues within peptides, see European Patent Application 0389180, herein incorporated by reference. Accordingly, radiolabeled PYY analogs can be used for imaging PYY receptors, e.g., for imaging cells containing PYY receptors.

The symbol X, Y, Z, $A^{22}$, $A^{23}$, $A^{24}$, and the like; and Ser, Leu or the like, as found in a peptide sequence herein stands for an amino acid residue, i.e., ═N—CH(R)—CO— when it is at the N-terminus, or —NH—CH(R)—CO—N═ when it is at C-terminus, or —NH—CH(R)—CO— when it is not at the N— or C-terminus, where R denotes the side chain (or identifying group) of an amino acid or its residue. For example, R is —$CH_2$COOH for Asp, R is —H for Gly, R is —$CH_2$OH for Ser, R is —$CH_3$ for Ala and R is —$CH_2CH_2CH_2CH_2NH_2$ for Lys. Also, when the amino acid residue is optically active, it is the L-form configuration that is intended unless the D-form is expressly designated.

As set forth above and for convenience in describing this invention, the conventional and nonconventional abbreviations for the various amino acids are used. They are familiar to those skilled in the art; but for clarity are listed below. All peptide sequences mentioned herein are written according to the usual convention whereby the N-terminal amino acid is on the left and the C-terminal amino acid is on the right. A short line between two amino acid residues indicates a peptide bond.

Asp=D=Aspartic Acid
Ala=A=Alanine
Arg=R=Arginine
Asn=N=Asparagine
Cys=C=Cysteine
Gly=G=Glycine
Glu=E=Glutamic Acid
Gln=Q=Glutamine
His=H=Histidine
Ile=I=Isoleucine
Leu=L=Leucine
Lys=K=Lysine
Met=M=Methionine
Phe=F=Phenylalanine
Pro=P=Proline
Ser=S=Serine
Thr=T=Threonine
Trp=W=Tryptophan
Tyr=Y=Tyrosine
Val=V=Valine
Orn=Ornithine
Nal=2-napthylalanine
Nva=Norvaline
Nle=Norleucine
Thi=2-thienylalanine
Pcp=4-chlorophenylalanine
Bth=3-benzothienyalanine
Bip=4,4'-biphenylalanine
Tic=tetrahydroisoquinoline-3-carboxylic acid
Aib=aminoisobutyric acid
Anb=α-aminonormalbutyric acid
Dip=2,2-diphenylalanine
Thz=4-Thiazolylalanine The compounds of the present invention can be provided in the form of pharmaceutically acceptable salts. Examples of preferred salts are those with therapeutically acceptable organic acids, e.g., acetic, lactic, maleic, citric, malic, ascorbic, succinic, benzoic, salicylic, methanesulfonic, toluenesulfonic, trifluoroacetic, or pamoic acid, as well as polymeric acids such as tannic acid or carboxymethyl cellulose, and salts with inorganic acids, such as hydrohalic acids, e.g., hydrochloric acid, sulfuric acid, or phosphoric acid and the like.

In another aspect, the invention features one of the above compounds and a pharmaceutically acceptable carrier substance in a therapeutic composition capable of decreasing excess intestinal water and electrolyte secretion.

In preferred embodiments, the composition is in the form of a liquid, pill, tablet, or capsule for oral administration; a liquid capable of being administered nasally as drops or spray or a liquid for intravenous, subcutaneous, parenteral, intraperitoneal or rectal administration. The therapeutic composition can also be in the form of an oil emulsion or dispersion in conjunction with a lipophilic salt such as pamoic acid, or in the form of a biodegradable sustained-release composition for subcutaneous or intramuscular administration. For maximum efficacy, zero-order release is desired.

In another aspect the invention features, a method for decreasing excess intestinal water and electrolyte secretion in a mammal, the method comprising administering to the mammal, e.g., a human, a therapeutically effective amount of the above mentioned compounds.

In addition, the invention features a method of regulating cell proliferation in a mammal, the method comprising administering to the mammal a therapeutically effective amount of the composition of the above mentioned compounds. Preferably, the method regulates the proliferation of an intestinal cell.

The invention also features methods for increasing nutrient transport, regulating lipolysis, and regulating blood flow in a mammal, the methods comprising administering to the mammal a therapeutically effective amount of the above mentioned compositions.

The compounds of the invention exhibit a broad range of biological activities related to their antisecretory and antimotility properties. The compounds are believed to suppress gastrointestinal secretions by direct interaction with epithelial cells or, perhaps, by inhibiting secretion of hormones or neurotransmitters which stimulate intestinal secretion. The compounds of the invention may also control intestinal blood flow which in turn may modulate intestinal hydrostatic pressure in favor of net water absorption.

The compounds of the invention are especially useful in the treatment of any number of gastrointestinal disorders (see e.g., *Harrison's Principles of Internal Medicine*, McGraw-Hill Inco, New York, 12th Ed.) that are associated with excess intestinal electrolyte and water secretion as well as decreased absorption, e.g., infectious (e.g., viral or bacterial) diarrhea, inflammatory diarrhea, short bowel syndrome, or the diarrhea which typically occurs following surgical procedures, e.g., ileostomy. Examples of infectious diarrhea include, without limitation, acute viral diarrhea, acute bacterial diarrhea (e.g., salmonella, campylobacter, and clostridium or due to protozoal infections), or traveller's diarrhea (e.g., Norwalk virus or rotavirus). Examples of inflammatory diarrhea include, without limitation, malabsorption syndrome, tropical spue, chronic pancreatitis, Crohn's disease, diarrhea, and irritable bowel syndrome. It has also been discovered that the peptides of the invention can be used to treat an emergency or life-threatening situation involving a gastrointestinal disorder, e.g., after surgery or due to cholera. Furthermore, the compounds of the invention can be used to treat patients suffering from Acquired Immune Deficiency Syndrome (AIDS), especially during cachexia.

The compounds of the invention are also useful for inhibiting small intestinal fluid and electrolyte secretion, augmenting nutrient transport—as well as increasing cell proliferation—in the gastrointestinal tract, regulating lipolysis in, e.g., adipose tissue, and regulating blood flow in a mammal.

The compounds of the invention are advantageous because they are truncated versions of the natural PYY peptide; thus, the shorter peptide not only facilitates easier synthesis and purification of the compounds, but also improves and reduces manufacturing procedures and expenses. Moreover, a shorter PYY compound is advantageous because such peptides will interact solely with PYY receptors and not with homologous receptors such as NPY Y1 and Y3; thus, minimizing unwanted agonist or antagonist side reactions.

Other features and advantages of the invention will be apparent from the following description of the preferred embodiments thereof, and from the claims.

DETAILED DESCRIPTION

The drawings will first be described.

DRAWINGS

Figure 1:
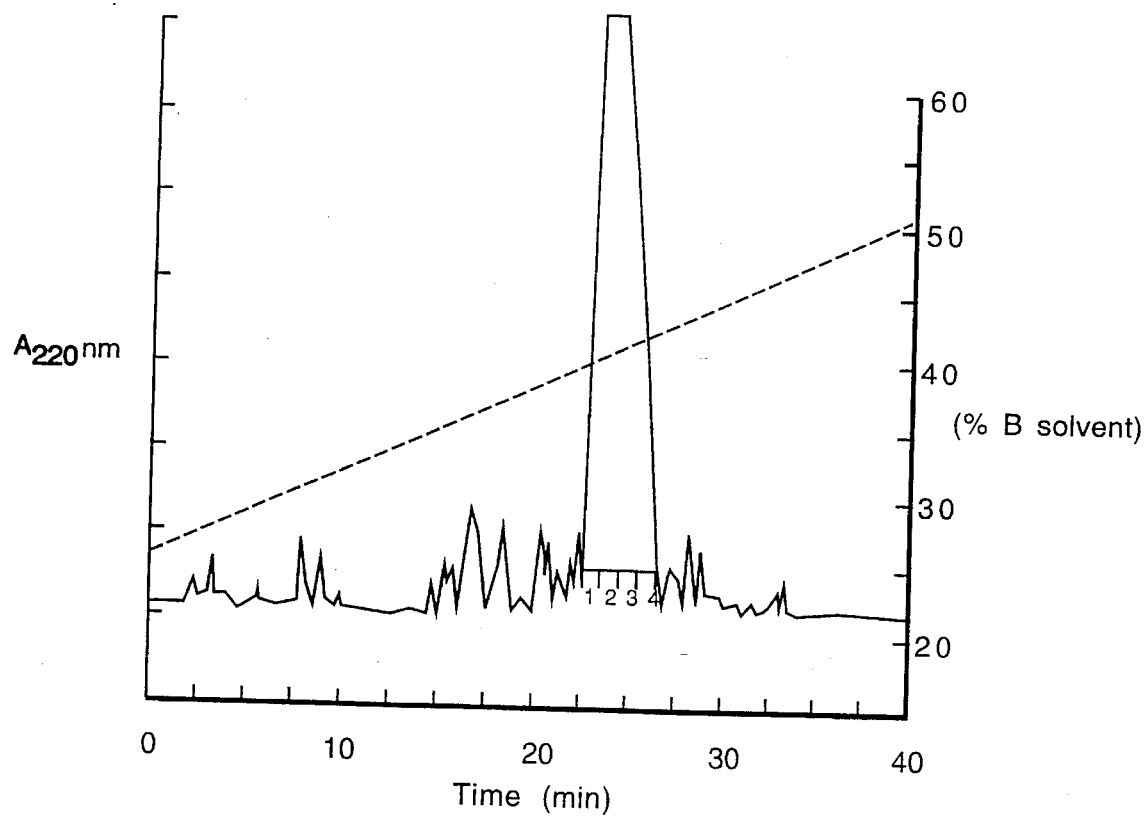

FIG. 1 shows a semipreparative reversed phase chromatogram of N-α-Ac-[Phe$^{27}$]PYY(22–36) (SEQ. ID. NO. 3) (≈25mg) obtained by HF cleavage. Conditions: Vydac C18 semipreparative column (250×10 mm, 300 Å pore size, 10 micron particle size); flow rate 4.7 ml/min; fractions 1, 2, 3, and 4 were collected and analyzed by analytical chromatography. The homogeneous fractions (1–3) were combined and dried in a speed vac.

Figure 2:
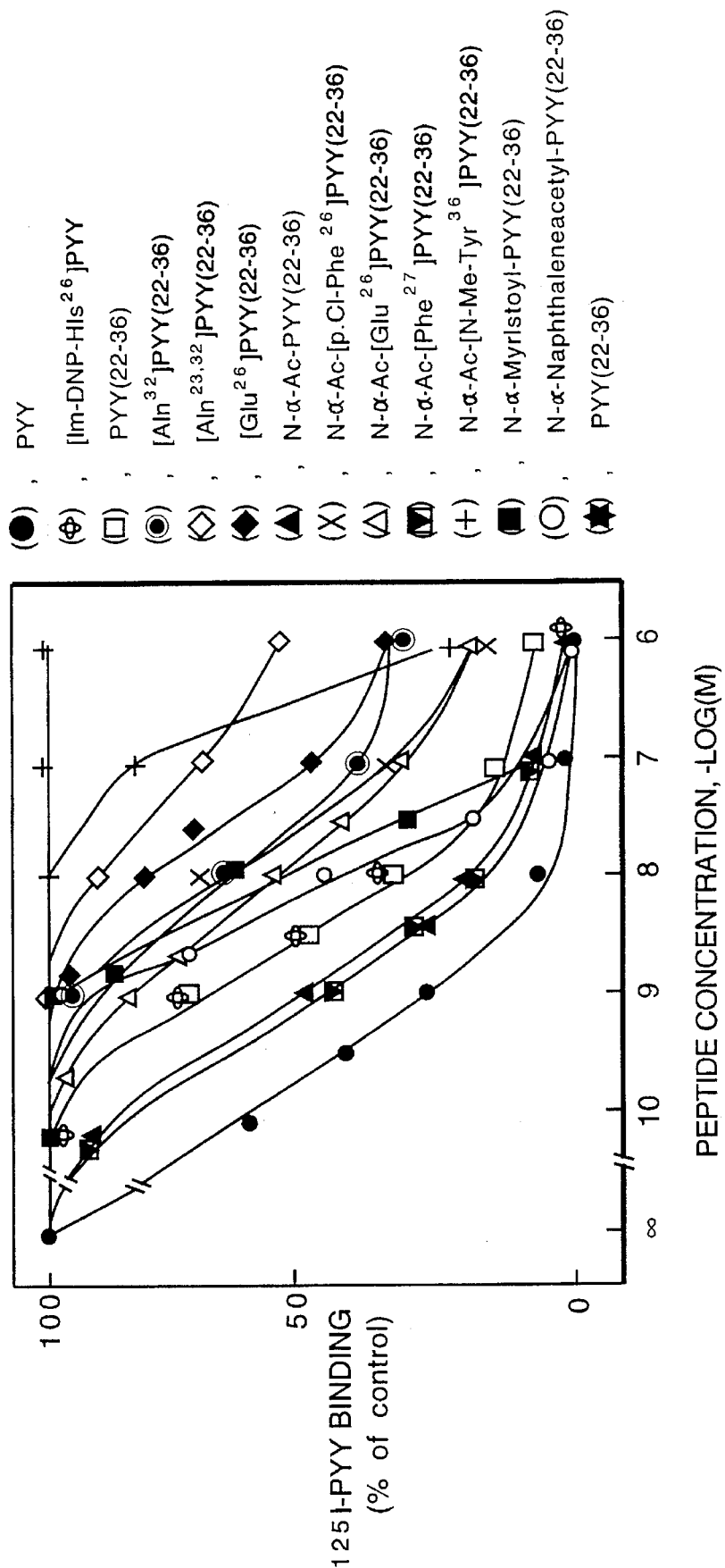

FIG. 2 shows a graph of the inhibition of $^{125}$I-PYY binding to rat jejunal membranes by increasing concentrations of PYY (SEQ. ID. NO. 1), PYY (22–36) (SEQ. ID. NO. 10), [Im-DNP-His$^{26}$]PYY (SEQ. ID. NO. 9), [Ala$^{32}$]PYY(22–36) (SEQ. ID. NO. 11), [Ala$^{23,32}$]PYY(22–36) (SEQ. ID. NO. 12), [Glu$^{28}$]PYY(22–36) (SEQ. ID. NO. 13), N-α-Ac-PYY(22–36) (SEQ. ID. NO. 14), N-α-Ac-[p.Cl-Phe$^{28}$]PYY(22–36) (SEQ. ID. NO. 15), N-α-Ac-[Glu$^{26}$]PYY(22–36) (SEQ. ID. NO. 16), N-α-Ac-[Phe$^{27}$]PYY(22–36) (SEQ. ID. NO. 3), N-α-Ac-[N-Me-Tyr$^{26}$]PYY(22–36) (SEQ. ID. NO. 17), N-α-Myristoyl-PYY (22–36) (SEQ. ID. NO. 18), N-α-Naphthaleneacetyl-PYY(22–36) (SEQ. ID. NO. 19), and PYY (22–26)(SEQ. ID. NO. 10).

Figure 3A:
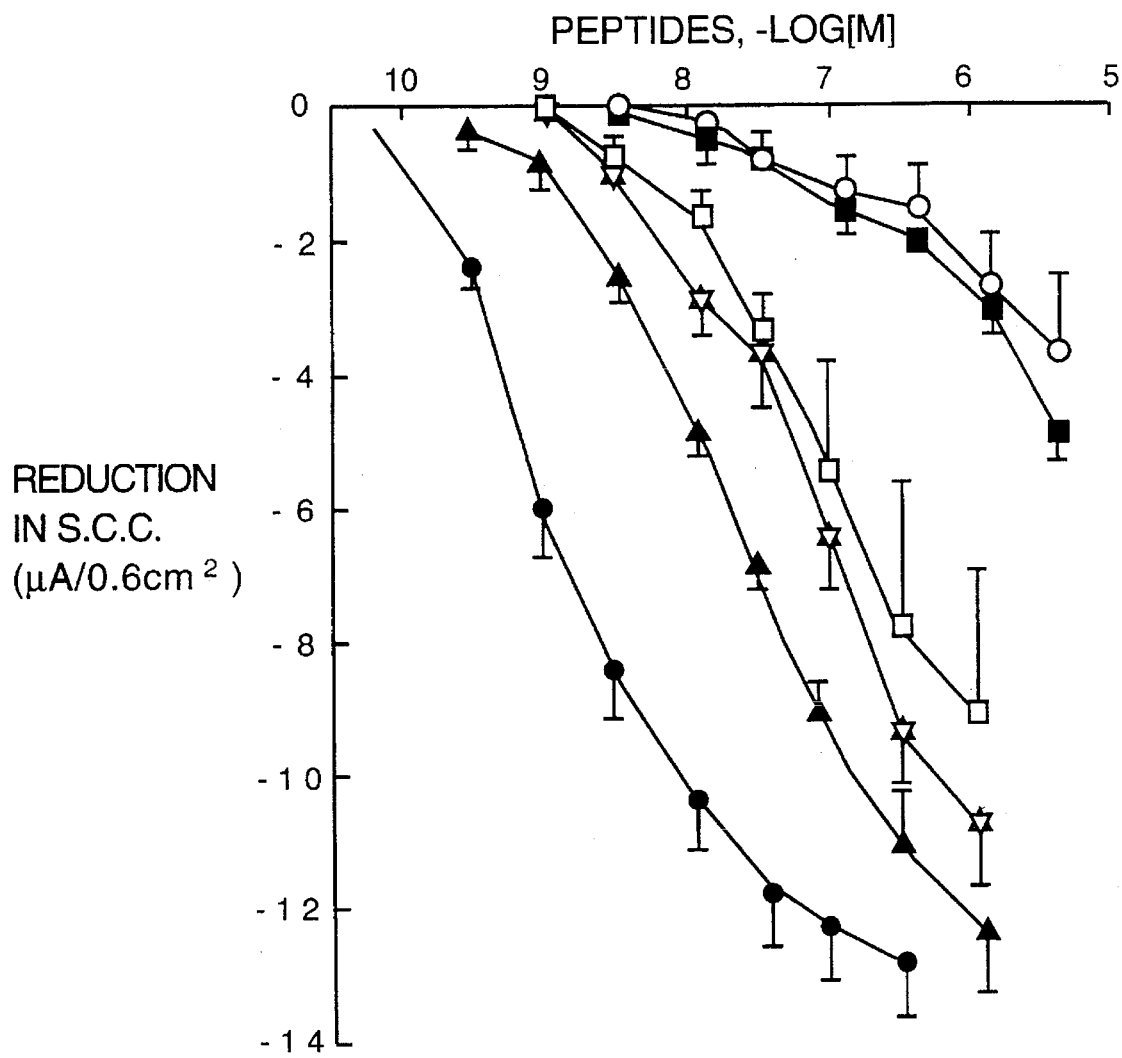
Figure 3B:
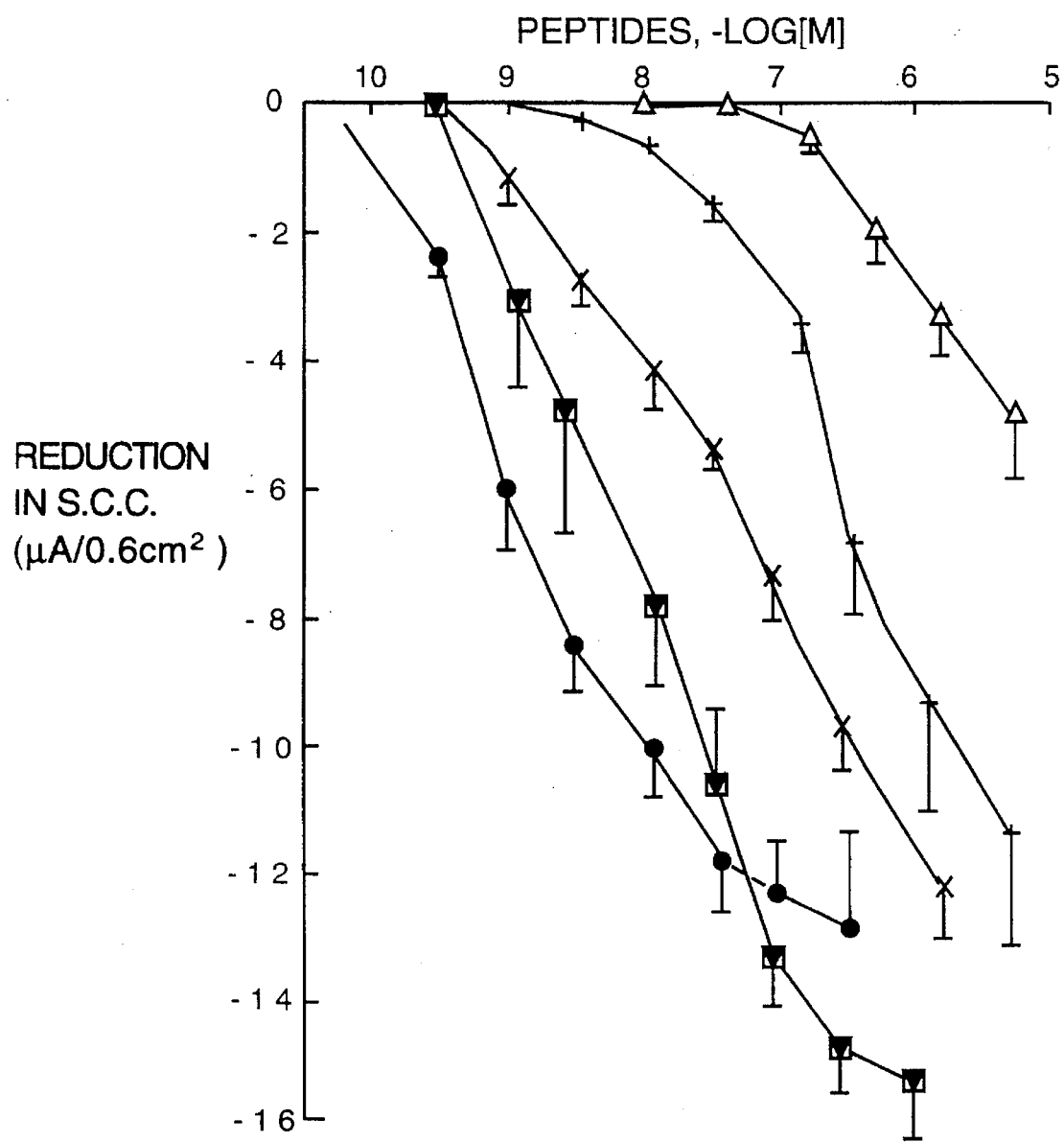

FIGS. 3A–3B show the antisecretory effects of PYY (SEQ. ID. NO. 1), PYY(22–36)(SEQ. ID. NO. 10) and analogs up one baseline short circuit current (SCC) in voltage clamped preparation of rat jejunum. Values of changes in SCC are quoted of μA/0.6 cm$^2$, mean ±SEM from between 3 and 7 different jejunal preparations. Peptides shown in A and B are denoted by the same symbol as in FIG. 2.

Figure 4:
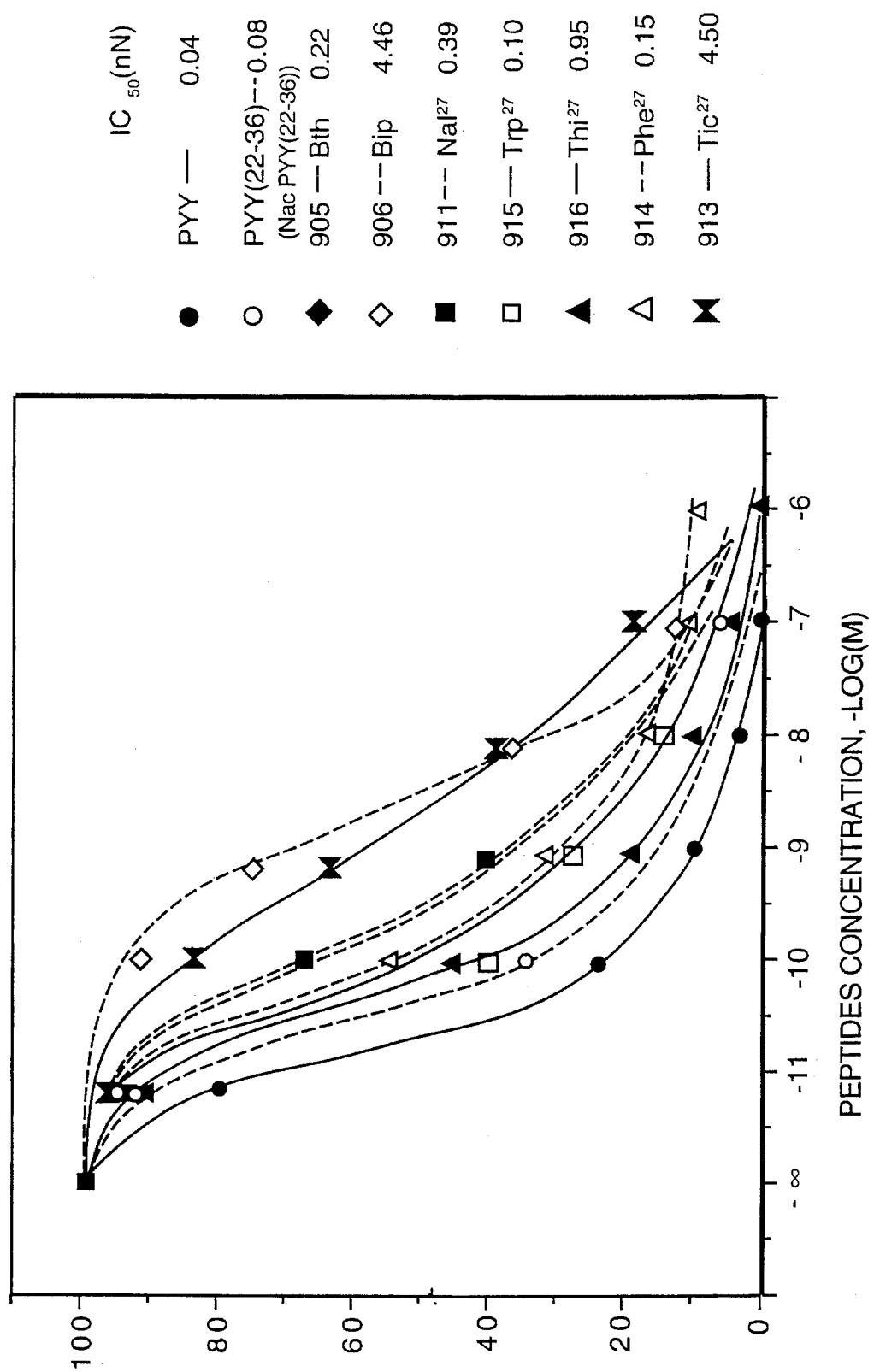

FIG. 4 shows a graph of the inhibition of $^{125}$I-PYY binding to rat jejunal membranes by increasing concentrations of PYY, N-α-Ac-PYY(22–36) (SEQ. ID. NO. 14), N-α-Ac-[Tic$^{27}$]PYY(22–36) (SEQ. ID. NO. 25), N-α-Ac-[Bip$^{27}$]PYY(22–36) (SEQ. ID. NO. 22), N-α-Ac-[Nal$^{27}$]PYY(22–36) (SEQ. ID. NO. 23), N-α-Ac-[Bth$^{27}$]PYY(22–36) (SEQ. ID. NO. 21), N-α-Ac-[Phe$^{27}$]PYY(22–36) (SEQ. ID. NO. 3), N-α-Ac-[Phe$^{27}$]PYY(25–36) (SEQ. ID. NO. 26), N-α-Ac-[Trp27]PYY (22–36) (SEQ. ID. NO. 5), and N-α-Ac-[Thi$^{27}$]PYY(22–36) (SEQ. ID. NO. 6).

There now follows a description of the synthesis, analysis for biological efficacy and use of the preferred embodiments of the invention. In order to determine the structural requirements necessary to elicit antisecretory effects, several analogs of the PYY active site, PYY(22–36), were synthesized and their binding and antisecretory potencies in rat jejunum were compared.

We now describe the structure, synthesis, and use of preferred embodiments of the invention.

STRUCTURE

The peptides of the invention have the general formula recited in the Summary of the Invention above. They all have an aromatic amino acid group at position 27 which is important for both antisecretory activity and utility as antidiarrheal compounds.

SYNTHESIS

The peptides of the present invention may be synthesized by any techniques that are known to those skilled in the peptide art. An excellent summary of the many techniques so available may be found in *Solid Phase Peptide Synthesis* 2nd ed. (Stewart, J. M. and Young, J. D. Pierce Chemical Company, Rockford, Ill., 1984).

The peptides listed in Table 1 and Table 2 were synthesized as follows. Peptide synthesis was performed on an Applied Biosystems Model 430A synthesizer. Amino acid and sequence analyses were carried out using Waters Pico-Tag and Applied Biosystems Model 470A instruments, respectively. Peptides were purified using a Waters Model 600 solvent delivery system equipped with a Model 481 Spectrophotometer and U6K injector according to standard protocols. Peptide masses were determined at the University of Michigan, Protein Chemistry Facility, Ann Arbor, Mich. according to standard methods. All Boc-L-amino acid derivatives, solvents, chemicals and the resins were obtained commercially and used without further purification.

Paramethylbenzhydroxylamine (MBHA) resin (0.45 mmol, —NH$_2$) was placed in the reaction vessel of the peptide synthesizer and the protected amino acid derivatives were sequentially coupled using the program provided by the manufacturers modified to incorporate a double coupling procedure (see, e.g., Balasubramaniam et al., *Peptide Research* 1: 32, 1988). All amino acids were coupled using 2.2 equivalents of preformed symmetrical anhydrides. Arg, Gln and Asn, however, were coupled as preformed 1-hydroxybenzotriazole (HOBT) esters to avoid side reactions.

At the end of the synthesis, the N-α-Boc group was removed and in some instances the free α-NH$_2$ was acetylated by reaction with acetic anhydride (2 equivalents) and diisopropyl ethylamine until a negative ninhydrin test was obtained (Anal. Biochem. 34:595, 1970). The peptide resin (~1.0 g) was then treated with HF (10 ml) containing p-cresol (~0.8 g) for 1 h at −2° to −4° C. The HF was evacuated and the residue was transferred to a fritted filter funnel with diethyl ether, washed repeatedly with diethyl ether, extracted with acetic acid (2×15 ml) and lyophilized. The crude peptides thus obtained were purified by semipreparative RP-HPLC as shown in FIG. 1.

Examples of the synthesized analogs are:

| | |
|---|---|
| [im-DNP-His$^{26}$]PYY | |
| YPAKPEAPGEDASPEELSRYYASLR [im-DNP-His$^{26}$] | (SEQ. ID No. 9) |
| YLNLVTRQRY—NH$_2$ | |
| PYY(22–36) | |
| A S L R H Y L N L V T R Q R Y—NH$_2$ | (SEQ. ID No. 10) |
| [Ala$^{32}$]PYY | |
| A S L R H Y L N L V [Ala] R Q R Y—NH$_2$ | (SEQ. ID No. 11) |
| [Ala$^{23,32}$]PYY | |
| A [Ala] L R H Y L N L V [Ala] R Q R Y-NN$_2$ | (SEQ. ID No. 12) |
| [Glu$^{28}$]PYY(22–36) | |
| A S L R H Y [Glu] N L V T R Q R Y—NH$_2$ | (SEQ. ID No. 13) |
| N-α-Ac-PYY(22–36) | |
| N-α-Ac-A S L R H Y L N L V T R 0 R Y—NH$_2$ | (SEQ. ID No. 14) |
| N-α-Ac[p.Cl.Phe$^{26}$]PYY | |
| N-α-Ac-A S L R [p.Cl.Phe$^{26}$] Y L N L V T R Q R Y—NH$_2$ | (SEQ. ID No. 15) |
| N-α-Ac[Glu$^{28}$]PYY | |
| N-α-Ac-A S L R H Y [Glu] N L V T R Q R Y—NH$_2$ | (SEQ. ID No. 16) |
| N-α-Ac[Phe$^{27}$]PYY | |
| N-α-Ac-A S L R H [Phe] E N L V T R Q R [N—Me—Tyr]—NH$_2$ | (SEQ. ID No. 3) |
| N-α-Ac]8 N—Me—Tyr$^{36}$]PYY | |
| N-α-Ac-A S L R H Y E N L V T R 0 R [N—Me—Tyr]—NH$_2$ | (SEQ. ID No. 17) |
| N-α-myristoyl-PYY(2214 36) | |
| N-α-myristoyi-A S L R H Y L N L V T R Q R Y—NH$_2$ | (SEQ. ID No. 18) |
| N-α-naphthateneacetyl-PYY(22–36) | |
| N-α-naphthateneacetyl -A S L R H Y L N L V T R Q R Y—NH$_2$ | (SEQ. ID No. 19) |
| N-α-Ac[Phe$^{27}$]PYY | |
| N-α-Ac-A S L R H [Phe] E N L V T R 0 R [N—Me—Tyr]—NH$_2$ | (SEQ. ID No. 3) |
| N-α-Ac-PYY(22–36) | |
| N-α-Ac-A S L R H Y L N L V T R Q R Y—NH$_2$ | (SEQ. ID No. 20) |
| N-α-Ac-[Bth$^{27}$]PYY(22–36) | |
| N-α-Ac-A S L R H [Bth] L N L V T R Q R Y—NH$_2$ | (SEQ. ID No. 21) |
| N-α-Ac-[Bip$^{27}$]PYY(22–36) | (SEQ. ID No. 22) |
| N-α-Ac-A S L R H [Bip] L N L V T R Q R Y—NH$_2$ | (SEQ. ID No. 22) |
| N-α-Ac-[Nal$^{27}$]PYY(22–36) | |
| N-α-Ac-A S L R H [NaL] L N L V T R Q R Y—NH$_2$ | (SEQ. ID No. 23) |
| N-α-Ac-[Trp$^{27}$]PYY(22–36) | (SEG. ID No. 5) |
| N-α-Ac-A S L R H [Trp] L N L V T R Q R Y—NH$_2$ | (SEQ. ID No. 5) |
| N-α-Ac-[Thi$^{27}$]PYY(22–36) | |
| N-α-Ac-A S L R N [Thi] L N L V T R Q R Y—NH$_2$ | (SEQ. ID No. 6) |
| N-α-Ac-[Tic$^{27}$]PYY(22–36) | |
| N-α-Ac-A S L R H [Tic] L N L V T R Q R Y—NH$_2$ | (SEQ. ID No. 25) |
| N-α-Ac-[Phe$^{27}$]PYY(25–36) | |
| N-α-Ac-H [Phe] L N L V T R Q R Y—NH$_2$ | (SEQ. ID No. 26) |
| N-α-Ac-[Phe$^{27}$,Thi$^{36}$]PYY(22–36) | |
| M-α-Ac-A S L R H (Phel L N L V T R Q R [Thi]-NH$_2$ | (SEQ. ID No. 27) |
| N-α-Ac-[Thz$^{26}$, Phe$^{27}$]PYY(22–36) | |
| N-α-Ac-A S L R [Thz][Phe] L N L V T R q R Y—NH$_2$ | (SEQ. ID No. 28) |
| N-α-Ac.[Pcp$^{27}$]PYY(22–36) | |
| N-α-Ac-A S L R H [Pcp] L N L V T R Q R Y—NH$_2$ | (SEQ. ID No. 29) |
| N-α-Ac-[Ph$^{22,27}$]PYY(22–36) | |
| N-α-Ac- [Phe]S L R N [Phe] L N L V T R Q R Y—NH$_2$ | (SEQ. ID No. 30) |
| N-α-Ac-[Tyr$^{22}$, Phe$^{27}$] PYY(22–36) | |
| N-α-Ac-[Tyr] S L R H [Phe] L N L V T R Q R Y—NH$_2$ | (SEQ. ID No. 7) |
| N-α-Ac-[Trp$^{28}$]PYY(22–36) | |
| N-α-Ac- A S L R H Y [Trp] N L V T R Q R Y—NH$_2$ | (SEQ. ID No. 31) |
| N-α-Ac-[Trp$^{28}$]PYY(22–36) | |
| N-α-Ac- A S L R H Y L N [Trp] V T R Q R Y—NH$_2$ | (SEQ. ID No. 32) |
| N-α-Ac-[Ala$^{26}$, Phe$^{27}$]PYY(22–36) | |
| N-α-Ac- A S L R [Ala] [Phe] L N L V T R Q R Y—NH$_2$ | (SEQ. ID No. 33) |
| N-α-Ac-[Bth$^{27}$]PYY(22–36) | |
| N-α-Ac- A S L R H [Bth] L N L V T R Q R Y—NH$_2$ | (SEQ. ID No. 34) |
| N-α-Ac-[Phe$^{27}$]PYY(22–36) | |
| N-α-Ac- A S L R H [Phe] L N L V T R Q R Y—NH$_2$ | (SEQ. ID No. 35) |
| N-α-Ac-[Phe$^{27,36}$]PYY(22–36) | |
| N-α-Ac- A S L R H [Phe] L N L V T R Q R [Phe]-NH$_2$ | (SEQ. ID No. 36) |
| N-α-Ac-[Phe$^{27}$, D-Trp$^{32}$]PYY(22–36) | |
| N-α-Ac- A S L R H [Phe] L N L V [D-Trp] R Q R Y—NH$_2$ | (SEQ. ID No. 37) |

ANALYSIS

Binding Studies

Preparation of $^{125}$I-PYY labeled only at Tyr$^{36}$ and rat jejunal epithelial plasma membranes were performed according to standard methods (see, e.g., Laburthe et al. *Endocrinology*, supra; Servin et al. supra; Voisin et al. *Ann. N. Y. Acad. Sci.* 611:343, 1990). Binding experiments were conducted in a total volume of 0.25 ml 60 mM HEPES buffer, pH 7, containing 2% BSA, 0.1% bacitracin, 5 mM MgCl$_2$ and 0.05 nM $^{125}$I-PYY with or without competing peptides. Bound and free peptides were separated by centrifugation at 20,000×g for 10 min. Non-specific $^{125}$I-PYY binding was determined in the presence of 1 μM unlabeled PYY represented 10% of the total binding.

Short Circuit Current Measurements

The antisecretory effects of the peptides were investigated by measuring the short-circuit current (SCC) in rat jejunal mucosa mounted in a Ussing chamber and automatically voltage clamped as described by Cox et al. (*J. Physiol.* supra). Briefly, strips of mucosa were placed between two halves of perspex Ussing chambers (window size, 0.6 cm$^2$) containing oxygenated (95% O$_2$/5% CO$_2$) Krebs-Henseleit solution (NaCl, 117 mM, KCl 4.7 mM, CaCl$_2$, 2.5 mM; MgSO$_4$ 1.2 mM, NaHCO$_3$ 24.8 mM and glucose 11.1 mM), pH 7.4, 37° C. Routinely, four preparations of jejunum were obtained from each animal and these exhibited comparable potential differences and SCC, but they were not paired. Preparations were automatically voltage clamped using a W-P dual voltage clamp and the SCC displayed continuously on pen recorders. Once a stable baseline SCC was reached, peptides were added to the basolateral reservoir only, and cumulative concentration-response profiles constructed.

Data Analyses

All points in the binding experiments are the mean of at least three experiments performed in duplicate. For clarity, the SEMs in the binding experiments are not shown in FIG. 2, but were less than 10%. Values of changes in SCC are quoted as μA/0.6 cm$^2$ mean±1 SEM from between 3 and 7 different preparations. EC$_{50}$ values were calculated from pooled cumulative concentration—response curves using an iterative curve fitting program. Comparison of data groups (SCC recordings) were made using unpaired Student's t-tests where a p value <0.5 was considered statistically significant.

There now follows the results of the biological activities of the compounds of the invention (see Table 1 and Table 2). As described below, the tested compounds were assayed for purity and for their binding and antisecretory potencies in rat jejunum.

Purified peptides were found to be >96% homogeneous by analytical reversed phase chromatography and, in addition, had the expected amino acid composition and masses. For example, FIG. 1 shows the RP-HPLC chromatogram of N-α-Ac-[Phe$^{27}$]PYY(22–36)(SEQ. ID. NO. 3). The free peptides were further characterized by sequence analysis (see, Table 1 and Table 2). The overall yields of the peptides were in the range of 10% to 30%.

PYY,[im-DNP-His$^{26}$]PYY (SEQ. ID. NO. 9) and the analogs of PYY(22–36)(SEQ. ID. NO. 10) displaced $^{125}$I-PYY bound to rat jejunal epithelial plasma membranes in a concentration-dependent manner. Although [im-DNP-His$^{26}$]PYY (SEQ. ID. NO. 9) and PYY(22–36) (SEQ. ID. NO. 10) were 20-times less potent than PYY based on IC$_{50}$ values, they displayed the same maximal response as the intact hormone (FIG. 2, Table 1). Substitution of Thr$^{32}$ with Ala as in [Ala$^{32}$]PYY(22–36)(SEQ. ID. NO. 11) resulted in the lowering of the binding potency while the replacement of both Ser$^{23}$ and Thr$^{32}$ with Ala further reduced the receptor affinity. Also, introduction of a negative charge at position 28 without altering the helicity as in [Glu$^{28}$]PYY(22–36)(SEQ. ID. NO. 13) decreased the binding possibly due to the disruption of the ionic interactions. Since the culated EC$_{50}$ values are listed in Table 1. The PYY(22–36) (SEQ. ID. NO. 10) analogs were generally less potent as antisecretory agents than as inhibitors of binding. The order of analog potency was similar to that from binding studies with two notable exceptions, namely N-α-myristoyl-PYY(22–36) (SEQ. ID. NO. 18) and N-α-naphthaleneacetyl-PYY(22–36) (SEQ. ID. NO. 19). N-α-acetylation and substitution of Tyr$^{27}$ with Phe increased the antisecretory potency of PYY(22–36) and this analog, N-α-Ac-[Phe$^{27}$]PYY(22–36) (SEQ. ID. NO. 3), was only 9-times less potent than the intact hormone. Furthermore, there was no significant difference between the maximal inhibitory responses, these being −12.6±2.4 and −12.0±1.3 μA/0.6 cm$^2$ for PYY (440 nM, n=6) (SEQ. ID. NO. 1) and N-α-Ac-[Phe$^{27}$]PYY(22–36) (1.4 μM, n=7) (SEQ. ID. NO. 3), respectively.

TABLE 1

Comparison of the binding and antisecretory potencies of PYY, fragments and their analogs

| PEPTIDES RT$^a$ NH+ (Calc.) | BINDING$^b$ (min) | SCC$^b$ | IC$_{50}$(nM) | EC$_{50}$(nM) |
|---|---|---|---|---|
| PYY (SEQ. ID. NO. 1) | 4.8 | 4240.2 (4241.7) | 0.2 | 1.7 |
| NPY (SEQ. ID. NO. 24) | 34.0$^c$ | 4253.8 (4254.7) | 2.0 | 9$^d$ |
| [im-DNP-His$^{26}$]PYY (SEG. ID. NO. 9) | 8.7$^c$ | 4406.9 (4407.8) | 4.0 | 72 |
| PYY(22–36) (SEQ. ID. NO. 10) | 4.4 | 1888.8 (1890.2) | 4.0 | 77 |
| [Ala$^{32}$]PYY(22–36) (SEQ. ID. NO. 11) | 4.7 | 1858.8 (1860.2) | 71 | n.d. |
| [Ala$^{23,32}$]PYY(22–36) (SEQ. ID. NO. 12) | 4.3 | 1842.8 (1844.2) | >10,000 | n.d. |
| [Glu$^{28}$]PYY(22–36) (SEQ. ID. NO. 13) | 3.8 | 1905.1 (1906.2) | 199 | n.d. |
| N-α-Ac-PYY(22–36) (SEQ. ID. NO. 14) | 10.0 | 1930.9 (1932.2) | 1.12 | 40 |
| N-α-Ac-[p.ClPhe$^{26}$]PYY(22–36) (SEQ. ID. NO. 15) | 14.9$^c$ | 1975.4 (1976.7) | 50 | 124 |
| N-α-Ac-[Glu$^{28}$]PYY(22–36) (SEQ. ID. NO. 16) | 3.9 | 1947.0 (1948.2) | 44.7 | 3,000 |
| N-α-Ac-[N—Me—Tyr$^{36}$]PYY(22–36) (SEQ. ID. NO. 17) | 13.5 | 1945.3 (1946.3) | 354 | 792 |
| N-α-Ac-[Phe$^{27}$]PYY(22–36) (SEQ. ID. NO. 3) | 8.3 | 1915.3 (1916.2) | 0.80 | 15.1 |
| N-α-Myristoyl-PYY(22–36) (SEQ. ID. NO. 18) | 4.8 1 | 2099.0 (2100.6) | 17.8 | 3,300 |
| N-α-Naphthateneacetyt-PYY(22–36) (SEQ. ID. NO. 19) | 17.0 | 2056.9 (2058.4) | 8.9 | 19,500 |

$^a$isocratic, 27% CH$_3$CN containing 0.1% TFA;
$^b$mean of three separate experiments;
$^c$isocratic, 32% CH$_3$CN containing 0.1% TFA;
$^d$from reference 10;
n.d.: not determined hydrophobic groups are known to increase the interaction with the receptors (Balasubramaniam et al. *Biochem. Biophys. Res. Comm.* 137:1041, 1986), the binding of a N-α-myristoyl- and N-α-naphthaleneacetyl-derivatives of PYY(22–36) was also determined. Both these analogs exhibited slightly lower binding affinity than PYY(22–36)(SEQ. ID. NO. 10) possibly due to increased steric hinderance. On the other hand, N-α-acetylation of PYY(22–36) (SEQ. ID. NO. 14) increased the receptor affinity four times. Further structure-activity studies with N-α-Ac-PYY(22–36) (SEQ. ID. NO. 20) revealed that substitution of Tyr$^{36}$ with N-Me-Tyr or His$^{26}$ with p.Cl-Phe lowers the binding potency. However, replacement of Tyr$^{27}$ with Phe increased the receptor affinity by 28%. As a control, the binding of PYY(22–36)(SEQ. ID. NO. 10) and several of its analogs were also tested. However, none of these analogs inhibited the binding of $^{125}$I-PYY even at 10 μM.

In mucosal preparations of rat jejunum PYY(22–36) (SEQ. ID. NO. 10) analogs reduced the baseline SCC in a concentration dependent manner (FIG. 3A and B) and cal- N-α-myristoyl-PYY(22–36)(SEQ. ID. NO. 18) and N-α-naphthaleneacetyl-PYY(22–36) (SEQ. ID. NO. 19) analogs, in contrast to their moderate binding potency, exhibited poor antisecretory responses with threshold concentrations of about 20 nM and EC$_{50}$ values greater than 2 and 30 μM respectively. After a cumulative concentration of 7.4 μM, N-α-myristoyl-PYY(22–36) (SEQ. ID. NO. 18) reduced the basal SCC by −5.2±0.6 μA/0.6 cm$^2$ (n=7). Subsequent addition of PYY (100 nM) further reduced the SCC by −10.2±0.7 μA/0.6 cm$^2$ (n=7) and this was not significantly different from control responses to PYY(22–36) (SEQ. ID. NO. 10) could antagonize PYY responses, three tissues were treated with the analog (1 μM) and PYY concentration-response curves were constructed and compared with controls. The fragment reduced the basal current by −0.4±0.3 μA/0.6 cm$^2$ and the resultant PYY EC$_{50}$ value (4.4±1.2 nM, n=3) did not differ significantly from that of the nontreated controls (2.6±1.1 nM, n=3).

These results show that modification of the active site of PYY (SEQ. ID. NO. 1), PYY(22–36)(SEQ. ID. NO. 10), can lead to a substantial increase in both the binding and antisecretory potencies of this fragment. The key analogs in this series exhibited the following order of potency: PYY (SEQ. ID. NO. 1)>N-α-Ac-[Phe$^{27}$]PYY (22–36)(SEQ. ID. NO. 3)>N-α-Ac-PYY(22–36)(SEQ. ID. NO. 14)>PYY(22–36) (SEQ. ID. NO. 10). Furthermore, our investigations revealed that the hydroxyl groups of Ser$^{23}$ and Thr$^{32}$ as well as the imidazole group of His$^{26}$ are important for interaction with intestinal PYY-preferring receptors. Although there was, in general, a good correlation between the binding and antisecretory potencies of the analogs, there were also notable exceptions. N-α-myristoyl-PYY(22–36) (SEQ. ID. NO. 18) and naphthaleneacetyl-PYY(22–36) (SEQ. ID. NO. 19) analogs inhibited $^{125}$I-PYY binding with moderate potency, but exhibited poor antisecretory responses. This observation suggested that these analogs may be antagonists. However, prior pretreatment of jejunal membranes with these analogs failed to significantly alter the antisecretory responses to PYY and the reason for the discrepancy remains unclear at present.

Table 2 and FIG. 4 present the $IC_{50}$ values for additonal PYY(22–36) (SEQ. ID. NO. 10) and PYY (25–36) analogs. Based on the results presented in Table 2 the analogs in this series exhibited the following order of potency:
N-α-Ac-[Tic$^{27}$]PYY(22–36)(SEQ. ID. NO. 25)<N-α-Ac[Bip$^{27}$]PYY(22–36) (SEQ. ID. NO. 22)<N-α-Ac-[Nal$^{127}$] PYY(22–36) (SEQ. ID. NO. 23)<N-α-Ac-[Bth$^{27}$] PYY(22–36) (SEQ. ID. NO. 21)<N-α-Ac-[Phe$^{27}$] PYY(22–36) (SEQ. ID. NO. 3)<N-α-Ac-[Phe$^{27}$] PYY(25–36) (SEQ. ID. NO. 26)<N-α-Ac-[Trp$^{27}$] PYY(22–36) (SEQ. ID. NO. 5)<N-α-Ac-[Thi$^{27}$] PYY(22–36) (SEQ. ID. NO. 6)<N-α-Ac-PYY(22–36)(SEQ. ID. NO. 14)<PYY (SEQ. ID. NO. 1).

TABLE 2

Comparison of Receptor Binding Data for PYY and PYY analogs

| PEPTIDE NO. | Peptide Structure | $IC_{50}$ (nM) |
| --- | --- | --- |
|  | PYY (SEQ. ID. NO. 1) | 0.04 |
|  | N-α-Ac-PYY(22–36) (SEQ. ID. NO. 14) | 0.08 |
| 905 | N-α-AC-[Bth$^{27}$]PYY(22–36) (SEQ. ID. NO. 21) | 0.22 |
| 906 | N-α-Ac-[Bip$^{27}$]PYY(22-36) (SEQ. ID. NO. 22) | 4.46 |
| 911 | N-α-Ac-[Nal$^{27}$]PYY(22–36) (SEQ. ID. NO. 23) | 0.39 |
| 915 | N-α-Ac-[Trp$^{27}$]PYY(22–36) (SEQ. ID. NO. 5) | 0.10 |
| 916 | N-α-Ac-[Thi$^{27}$]PYY(22–36) (SEQ. ID. NO. 6) | 0.095 |
| 914 | N-α-Ac-[Phe$^{27}$]PYY(25–36) (SEQ. ID. NO. 26) | 0.15 |
| 913 | N-α-Ac-[Tic$^{27}$]PYY(22–36) (SEQ. ID. NO. 25) | 4.50 |

NPY/PYY receptors characterized to date have been broadly classified into Y-1, Y-2 and Y-3 subtypes (Balsubramaniam et al. *J. Biol. Chem.* 265:14724, 1990; Michel, *Trends Pharmacol. Sci.* 12:389, 1991). Both Y-1 and Y-2 receptors exhibit a preference for PYY over NPY, and more significantly C-terminal fragments of NPY and PYY are effective only at the Y-2 subtype. Y-3 receptors, on the other hand, exhibit a greater affinity for NPY than PYY. Since rat jejunal mucosa antisecretory responses show an order of agonist potency PYY (SEQ. ID. NO. 1)>NPY (SEQ. ID. NO. 24)>PYY(13–36)(SEQ. ID. NO. 32)>NPY(13–36)(SEQ. ID. NO. 33) these epithelial receptors are Y-2 like, and are completely insensitive to the Y-1 selective agonist [Pro$^{34}$]NPY (Cox et al. *Peptides*, supra). The results further describe N-α-Ac-PYY(22–36) (SEQ. ID. NO. 14) and N-α-Ac-[Phe$^{27}$]pyy(22–36)(SEQ. ID. NO. 3) to be more potent than PYY(22–36)(SEQ. ID. NO. 10) and the corresponding C-terminal fragments of NPY of varying lengths (Cox et al. *Br. J. Pharmacol.* supra). The higher affinity for PYY (SEQ. ID. NO. 1) and its C-terminal fragments compared with NPY (SEQ. ID. NO. 24) and its respective fragments is in agreement with the order of potency obtained from receptor binding studies with rat intestinal epithelial membranes (Laburthe et al. supra; Laburthe, supra; Voisin et al. *Ann. N.Y. Acad. Sci.* supra; Voisin et al. *Am. J. Physiol.*)

In addition, analogs listed in Table 3 were synthesized as described above and tested for binding activity. The results shown in Table 3 demonstrate that N-α-Ac-[TYr$^{22}$, Phe$^{27}$] PYY(22–36) (SEQ. ID. NO. 7) is similar in its competitive binding as PYY (SEQ. ID. NO. 1), indicating that the introduction of an aromatic amino acids e.g., Tyr, at position 22 is an effective PYY analog.

TABLE 3

| PEPTIDE NO. | Peptide Structure | $IC_{50}$ (nM) |
| --- | --- | --- |
|  | PYY (SEQ. ID. NO. 1) | 0.10 |
| 917 | N-α-Ac-[Phe$^{27}$, Thi$^{36}$]PYY(22–26) (SEQ. ID. NO. 27) | 4.46 |
| 918 | N-α-Ac-[Thz$^{26}$, Phe$^{27}$]PYY(22–36) (SEQ. ID. NO. 28) | 4.50 |
| 904 | N-α-Ac-[Pcp$^{27}$]PYY(22–36) (SEQ. ID. NO. 29) | 1.58 |
| 908 | N-α-Ac-[Phe$^{22,27}$]PYY(22–36) (SEQ. ID. NO. 30) | 11.22 |
| 910 | N-α-Ac-[Tyr$^{22}$, Phe$^{27}$]PYY(22–36) (SEQ. ID. NO. 7) | 0.10 |

USE

In the practice of the method of the present invention, an effective amount of an any one or combination of the analogs of the invention, e.g., N-α-Ac-[Phe$^{27}$]PYY(22–36) (SEQ. ID. NO. 3), N-α-Ac-[Trp$^{27}$]PYY(22–36) (SEQ. ID. NO. 24), N-α-Ac-[Phe$^{27}$]PYY(25–36) (SEQ. ID. NO. 3), N-α-Ac-[Thi$^{27}$]PYY(22–36) (SEQ. ID. NO. 6) or derivative thereof, is administered via any of the usual and acceptable methods known in the art, either singly or in combination with another compound or compounds of the present invention. These compounds or compositions can thus be administered orally (e.g., buccal cavity), sublingually, parenterally (e.g., intramuscularly, intravenously, or subcutaneously), rectally (e.g., by suppositories or washings), transdermally (e.g., skin electroporation) or by inhalation (e.g., by aerosol), and in the form or either solid, liquid or gaseous dosage, including tablets and suspensions. The administration can be conducted in a single unit dosage form with continuous therapy or in a single dose therapy ad libitum.

Thus, the method of the present invention is practiced when relief of symptoms is specifically required or perhaps imminent. Alternatively, the method of the present invention is effectively practiced as continuous or prophylactic treatment.

Useful pharmaceutical carriers for the preparation of the compositions hereof, can be solids, liquids or gases; thus, the compositions can take the form of tablets, pills, capsules, suppositories, powders, enterically coated or other protected formulations (e.g. binding on ion-exchange resins or packaging in lipid-protein vesicles), sustained release formulations, solutions, suspensions, elixirs, aerosols, and the like. The carrier can be selected from the various oils including those of petroleum, animal, vegetable or synthetic origin, e.g., peanut oil, soybean oil, mineral oil, sesame oil, and the like. Water, saline, aqueous dextrose, and glycols are preferred liquid carriers, particularly (when isotonic with the blood) for injectable solutions. For example, formulation for intravenous administration comprise sterile aqueous solutions of the active ingredient(s) which are prepared by dissolving solid active ingredient(s) in water to produce an aqueous solution, and rendering the solution sterile. Suitable pharmaceutical excipients include starch, cellulose, talc, glucose, lactose, talc, gelatin, malt, rice, flour, chalk, silica, magnesium stearate, sodium stearate, glycerol monostearate, sodium chloride, dried skim milk, glycerol, propylene glycol, water, ethanol, and the like. The compositions may be subjected to conventional pharmaceutical additives such as preservatives, stabilizing agents, wetting or emulsifying agents, salts for adjusting osmotic pressure, buffers and the like. Suitable pharmaceutical carriers and their formulation are described in *Remington's Pharmaceutical Sciences* by E. W. Martin. Such compositions will, in any event, contain an effective amount of the active compound together with a suitable carrier so as to prepare the proper dosage form for proper administration to the recipient.

The dose of the compound of the present invention for treating the above-mentioned disorders varies depending upon the manner of administration, the age and the body weight of the subject, and the condition of the subject to be treated, and ultimately will be decided by the attending physician or veterinarian. Such amount of the active compound as determined by the attending physician or veterinarian is referred to herein as a "therapeutically effective amount". Thus, a typical administration is oral administration or parenteral administration. The daily dose in the case of oral administration is typically in the range of 0.1 to 100 mg/kg body weight, and the daily dose in the case of parenteral administration is typically in the range of 0.001 to 50 mg/kg body weight.

To be effective for the prevention or treatment of gastroenterological disorders, especially infectious (e.g. viral or bacterial) or inflammatory diarrhea, or diarrhea resulting from surgery, it is important that the therapeutic agents be relatively non-toxic, non-antigenic and non-irritating at the levels in actual use.

It is understood that the examples and embodiments described herein are for illustrative purposes only and that various modifications or changes in light thereof will be suggested to persons skilled in the art and are to be included within the spirit and purview of this application and scope of the appended claims.

What is claimed is:

1. A compound having the formula:

$$R_2-X-A^{22}-A^{23}-A^{24}-A^{25}-A^{26}-A^{27}-A^{28}-A^{29}-A^{30}-$$
$$-A^{31}-A^{32}-A^{33}-A^{34}-A^{35}-A^{36}-R_4$$

with $R_1$ attached to the same nitrogen as $R_2$, and $R_3$ attached to $A^{36}$ wherein X is Cys or is deleted;

each of $R^1$ and $R^2$ is bonded to the nitrogen atom of the α-amino group of the N-terminal amino acid;

$R_1$ is H, $C_1$–$C_{12}$ alkyl, $C_6$–$C_{18}$ aryl, $C_1$–$C_{12}$ acyl, $C_7$–$C_{18}$ aralkyl, or $C_7$–$C_{18}$ alkaryl;

$R_2$ is H, $C_1$–$C_{12}$ alkyl, $C_6$–$C_{18}$ aryl, $C_1$–$C_{12}$ acyl, $C_7$–$C_{18}$ aralkyl, or $C_7$–$C_{18}$ alkaryl;

$A^{22}$ is an aromatic amino acid, Ala, Aib, Anb, N-Me-Ala, or is deleted;

$A^{23}$ is Ser, Thr, Ala, Aib, N-Me-Ser, N-Me-Thr, N-Me-Ala, D-Trp, or is deleted;

$A^{24}$ is Leu, Gly, Ile, Val, Trp, Nle, Nva, Aib, Anb, N-Me-Leu, or is deleted;

$A^{25}$ is Arg, Lys, homo-Arg, diethyl-homo-Arg, Lys-ε-NH—R (where R is H, a branched or straight chain $C_1$–$C_{10}$ alkyl group, or an aryl group), Orn, or is deleted;

$A^{26}$ is Ala, His, Thr, 3-Me-His, 1-Me-His, β-pyrozolylalanine, N-Me-His, Arg, Lys, homo-Arg, diethyl-homo-Arg, Lys-ε-NH—R (where R is H, a branched or straight chain $C_1$–$C_{10}$ alkyl group, or an aryl group), Orn, or is deleted;

$A^{27}$ is Nal, Bip, Pcp, Tic, Trp, Bth, Thi, or Dip;

$A^{28}$ is Leu, Val, Trp, Nle, Nva, Aib, Anb, or N-Me-Leu;

$A^{29}$ is Asn, Ala, Gln, Gly, Trp, or N-Me-Asn;

$A^{30}$ is Leu, Ile, Val, Trp, Nle, Nva, Aib, Anb, or N-Me-Leu;

$A^{31}$ is Val, Leu, Ile, Trp, Nle, Nva, Aib, Anb, or N-Me-Val;

$A^{32}$ is Thr, Ser, N-Me-Ser, N-Me-Thr, or D-Trp;

$A^{33}$ is Cys, Arg, Lys, homo-Arg, diethyl-homo-Arg, Lys-ε-NH—R (where R is H, a branched or straight chain $C_1$–$C_{10}$ alkyl group, or $C_6$–$C_{18}$ aryl group), or Orn;

$A^{34}$ is Cys, Gln, Asn, Ala, Gly, N-Me-Gln, Aib, or Anb;

$A^{35}$ is Cys, Arg, Lys, homo-Arg, diethyl-homo-Arg, Lys-ε-NH—R (where R is H, a branched or straight chain $C_1$–$C_{10}$ alkyl group, or $C_6$–$C_{18}$ aryl group), or Orn;

$A^{36}$ is an aromatic amino acid, or Cys;

$R_3$ is H, $C_1$–$C_{12}$ alkyl, $C_6$–$C_{18}$ aryl, $C_1$–$C_{12}$ acyl, $C_7$–$C_{18}$ aralkyl, or $C_7$–$C_{18}$ alkaryl;

$R_4$ is H, $C_1$–$C_{12}$ alkyl, $C_6$–$C_{18}$ aryl, $C_1$–$C_{12}$ acyl, $C_7$–$C_{18}$ aralkyl, or $C_7$–$C_{18}$ alkaryl, or a pharmaceutically acceptable salt thereof.

2. A compound having the formula:

$$R_2-A^{25}-A^{26}-A^{27}-A^{28}-A^{29}-A^{30}-A^{31}-A^{32}-A^{33}-$$
$$-A^{34}-A^{35}-A^{36}-R_4$$

with $R_1$ on the same nitrogen as $R_2$, and $R_3$ attached to $A^{36}$ wherein each of $R^1$ and $R^2$ is bonded to the nitrogen atom of the α-amino group of the N-terminal amino acid;

$R_1$ is H, $C_1$–$C_{12}$ alkyl, $C_6$–$C_{18}$ aryl, $C_1$–$C_{12}$ acyl, $C_7$–$C_{18}$ aralkyl, or $C_7$–$C_{18}$ alkaryl;

$R_2$ is H, $C_1$–$C_{12}$ alkyl, $C_6$–$C_{18}$ aryl, $C_1$–$C_{12}$ acyl, $C_7$–$C_{18}$ aralkyl, or $C_7$–$C_{18}$ alkaryl;

$A^{25}$ is Arg, Lys, homo-Arg, diethyl-homo-Arg, Lys-ε-NH—R (where R is H, a branched or straight chain $C_1$–$C_{10}$ alkyl group, or an aryl group), Orn, or is deleted;

$A^{26}$ is Ala, His, Thr, 3-Me-His, β-pyrozolylalanine, N-Me-His, Arg, Lys, homo-Arg, diethyl-homo-Arg, Lys-ε-NH—R (where R is H, a branched or straight chain $C_1$–$C_{10}$ alkyl group, or an aryl group), or Orn;

$A^{27}$ is an aromatic amino acid;

$A^{28}$ is Leu, Val, Trp, Nle, Nva, Aib, Aib, Anb, or N-Me-Leu;

$A^{29}$ is Asn, Ala, Gln, Gly, Trp, or N-Me-Asn;

$A^{30}$ is Leu, Ile, Val, Trp, Nle, Nva, Aib, Anb, or N-Me-Leu;

$A^{31}$ is Val, Leu, Ile, Trp, Nle, Nva, Aib, Anb, or N-Me-Val;

$A^{32}$ is Thr, Ser, N-Me-Ser, N-Me-Thr, or D-Trp;

$A^{33}$ is Arg, Lys, homo-Arg, diethyl-homo-Arg, Lys-ε-NH—R (where R is H, a branched or straight chain $C_1$–$C_{10}$ alkyl group, or $C_6$–$C_{18}$ aryl group), Cys, or Orn;

$A^{34}$ is Cys, Gln, Asn, Ala, Gly, N-Me-Gln, Aib, or Anb;

$A^{35}$ is Arg, Lys, homo-Arg, diethyl-homo-Arg, Lys-ε-NH—R (where R is H, a branched or straight chain $C_1$–$C_{10}$ alkyl group, or $C_6$–$C_{18}$ aryl group), Cys, or Orn;

$A^{36}$ is an aromatic amino acid, or Cys;

$R_3$ is H, $C_1$–$C_{12}$ alkyl, $C_6$–$C_{18}$ aryl, $C_1$–$C_{12}$ acyl, $C_7$–$C_{18}$ aralkyl, or $C_7$–$C_{18}$ alkaryl; and $R_4$ is H, $C_1$–$C_{12}$ alkyl, $C_6$–$C_{18}$ aryl, $C_1$–$C_{12}$ acyl, $C_7$–$C_{18}$ aralkyl, or $C_7$–$C_{18}$ alkaryl, or a pharmaceutically acceptable salt thereof.

3. A compound having the formula:

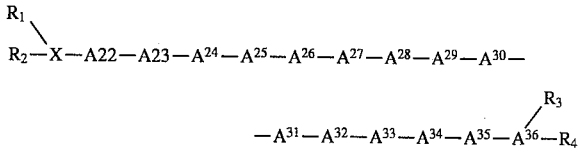

wherein

X is Cys or is deleted;

$R_1$ and $R_2$ are bonded to the N-terminal amino acid;

$R_1$ is H, $C_1$–$C_{12}$ alkyl, $C_6$–$C_{18}$ aryl, $C_1$–$C_{12}$ acyl, $C_7$–$C_{18}$ aralkyl, or $C_7$–$C_{18}$ alkaryl;

$R_2$ is H, $C_1$–$C_{12}$ alkyl, $C_6$–$C_{18}$ aryl, $C_1$–$C_{12}$ acyl, $C_7$–$C_{18}$ aralkyl, or $C_7$–$C_{18}$ alkaryl;

$A^{22}$ is an aromatic amino acid or is deleted;

$A^{23}$ is Ser, Thr, Ala, Aib, N-Me-Ser, N-Me-Thr, N-Me-Ala, D-Trp, or is deleted;

$A^{24}$ is Leu, Gly, Ile, Val, Trp, Nle, Nva, Aib, Anb, N-Me-Leu, or is deleted;

$A^{25}$ is Arg, Lys, homo-Arg, diethyl-homo-Arg, Lys-ε-NH—R (where R is H, a branched or straight chain $C_1$–$C_{10}$ alkyl group, or an aryl group), Orn, or is deleted;

$A^{26}$ is Ala, His, Thr, 3-Me-His, 1-Me-His, β-pyrozolylalanine, N-Me-His, Arg, Lys, homo-Arg, diethyl-homo-Arg, Lys-ε-NH—R (where R is H, a branched or straight chain $C_1$–$C_{10}$ alkyl group, or an aryl group), or Orn;

$A^{27}$ is an aromatic amino acid other than Tyr;

$A^{28}$ is Leu, Val, Trp, Nle, Nva, Aib, Anb, or N-Me-Leu;

$A^{29}$ is Asn, Ala, Gln, Gly, Trp, or N-Me-Asn;

$A^{30}$ is Leu, Ile, Val, Trp, Nle, Nva, Aib, Anb, or N-Me-Leu;

$A^{31}$ is Val, Leu, Ile, Trp, Nle, Nva, Aib, Anb, or N-Me-Val;

$A^{32}$ is Thr, Ser, N-Me-Ser, N-Me-Thr, or D-Trp;

$A^{33}$ is Cys, Arg, Lys, homo-Arg, diethyl-homo-Arg, Lys-ε-NH—R (where R is H, a branched or straight chain $C_1$–$C_{10}$ alkyl group, or $C_6$–$C_{18}$ aryl group), or Orn;

$A^{34}$ is Cys, Gln, Asn, Ala, Gly, N-Me-Gln, Aib, or Anb;

$A^{35}$ is Cys, Arg, Lys, homo-Arg, diethyl-homo-Arg, Lys-ε-NH—R (where R is H, a branched or straight chain $C_1$–$C_{10}$ alkyl group, or $C_6$–$C_{18}$ aryl group), or Orn;

$A^{36}$ is an aromatic amino acid, or Cys;

$R_3$ is H, $C_1$–$C_{12}$ alkyl, $C_6$–$C_{18}$ aryl, $C_1$–$C_{12}$ acyl, $C_7$–$C_{18}$ aralkyl, or $C_7$–$C_{18}$ alkaryl;

$R_4$ is H, $C_1$–$C_{12}$ alkyl, $C_6$–$C_{18}$ aryl, $C_1$–$C_{12}$ acyl, $C_7$–$C_{18}$ aralkyl, or $C_7$–$C_{18}$ alkaryl, or a pharmaceutically acceptable salt thereof.

4. The compound of claim 1, wherein said compound has the formula:

N-α-Ac-Ala-Ser-Leu-Arg-His-Trp-Leu-Asn-Leu-Val-Thr-Arg-Gln-Arg-Tyr-NH$_2$ (SEQ. ID. NO. 5), or a pharmaceutically acceptable salt thereof.

5. The compound of claim 1, wherein said compound has the formula:

N-α-Ac-Ala-Ser-Leu-Arg-His-Thi-Leu-Asn-Leu-Val-Thr-Arg-Gln-Arg-Tyr-NH$_2$ (SEQ. ID. NO. 6), or a pharmaceutically acceptable salt thereof.

6. The compound of claim 3, wherein said compound has the formula:

N-α-Ac-Tyr-Ser-Leu-Arg-His-Phe-Leu-Asn-Leu-Val-Thr-Arg-Gln-Arg-Tyr-NH$_2$ (SEQ. ID. NO. 7), or a pharmaceutically acceptable salt thereof.

7. The compound of claim 2, wherein $A^{27}$ is Phe, Nal, Bip, Pcp, Tic, Trp, Bth, Thi, or Dip.

8. The compound of claim 7, wherein said compound has the formula:

N-α-Ac-Arg-His-Phe-Leu-Asn-Leu-Val-Thr-Arg-Gln-Arg-TYr-NH$_2$ (SEQ. ID. NO. 26), or a pharmaceutically acceptable salt thereof.

9. A therapeutic composition capable of decreasing excess intestinal water and electrolyte secretion, said composition comprising a therapeutically effective amount of the compound of claim 1 or claim 2, together with a pharmaceutically acceptable carrier substance.

10. A method of decreasing excess intestinal water and electrolyte secretion in a mammal in need of such treatment, said method comprising administering to said mammal a therapeutically effective amount of the compound of claim 1, claim 2, or claim 3, together with a pharmaceutically acceptable carrier substance.

11. A method of regulating cell proliferation in a mammal in need of such treatment, said method comprising administering to said mammal a therapeutically effective amount of the compound of claim 1, claim 2, or claim 3, together with a pharmaceutically acceptable carrier substance.

12. A method of augmenting nutrient transport in a mammal in need of such treatment, said method comprising administering to said mammal a therapeutically effective amount of the compound of claim 1, claim 2, or claim 3, together with a pharmaceutically acceptable carrier substance.

13. A method of regulating lipolysis in a mammal in need of such treatment, said method comprising administering to said mammal a therapeutically effective amount of the compound of claim 1, claim 2, or claim 3, together with a pharmaceutically acceptable carrier substance.

14. A method of regulating blood flow in a mammal in need of such treatment, said method comprising administering to said mammal a therapeutically effective amount of the compound of claim 1, claims 2, or claim 3, together with a pharmaceutically acceptable carrier substance.

15. A dimeric compound comprising either two peptides of claim 1, claim 2, or claim 3, one peptide of claim 1 and one peptide of claim 2; one peptide of claim 1 and one peptide of claim 3; or one peptide of claim 2 and one peptide of claim 3; wherein said dimer is formed by either an amide bond or a disulfide bridge between said two peptides.

16. The compound of claim 3, wherein $A^{27}$ is Phe, Nal, Bip, Pcp, Tic, Trp, Bth, Thi, or Dip.

17. The compound of claim 3, wherein said compound has the formula: N-α-Ac-Phe-Ser-Leu-Arg-His-Phe-Leu-Asn-Leu-Val-Thr-Arg-Gln-Arg-Tyr-NH$_2$ (SEQ ID NO:30).

18. The compound of claim 1, wherein the —CO—NH— bond between the residues $A^{28}$ and $^{29}$, $A^{29}$ and $A^{30}$, $A^{30}$ and $A^{31}$, $A^{31}$ and $A^{32}$, $A^{33}$ and $A^{34}$, $A^{34}$ and $A^{35}$, or $A^{35}$ and $A^{36}$ is replaced with $CH_2$—NH, $CH_2$—S, $CH_2$—$CH_2$, or $CH_2$—O.

19. The compound of claim 18, wherein the CO—NH bond between the residues $A^{35}$ and $A^{36}$ is replaced with $CH_2$—NH.

20. A compound of claim 1, wherein

X is deleted;
$A^{22}$ is an aromatic amino acid, Ala, Aib, Anb, or deleted;
$A^{23}$ is Ser, Thr, D-Trp, or deleted;
$A^{24}$ is Leu, Gly, Ile, Val, Nle, Nva, Aib, Anb, or deleted;
$A^{25}$ is Arg, homo-Arg, diethyl-homo-Arg, or deleted;
$A^{26}$ is Ala, His, 3-Me-His, 1-Me-His, or deleted;
$A^{28}$ is Leu, Val, Trp, Nle, Nva, Aib, or Anb;
$A^{29}$ is Asn, Gln, or Trp;
$A^{30}$ is Leu, Ile, Val, Trp, Nle, Nva, Aib, or Anb;
$A^{31}$ is Val, Leu, Ile, Nle, Nva, Aib, or Anb;
$A^{32}$ is Thr, Ser, or D-Trp;
$A^{33}$ is Arg, homo-Arg, or diethyl-homo-Arg;
$A^{34}$ is Gln or Asn;
$A^{35}$ is Arg, homo-Arg, or diethyl-homo-Arg; and
$A^{36}$ is an aromatic amino acid.

21. A compound of claim 20, wherein
$A^{22}$ is Tyr, Phe, Ala, or deleted;
$A^{23}$ is Ser, D-Trp, or deleted;
$A^{24}$ is Leu, Gly, Nle, or deleted;
$A^{25}$ is Arg, or deleted;
$A^{26}$ is Ala, His, or deleted;
$A^{28}$ is Leu, Trp, or Nle;
$A^{29}$ is Asn, or Trp;
$A^{30}$ is Leu, Trp, or Nle;
$A^{31}$ is Val or Anb;
$A^{39}$ is Thr, or D-Trp;
$A^{33}$ is Arg;
$A^{34}$ is Gln;
$A^{35}$ is Arg; and
$A^{36}$ is Tyr, or Phe.

22. A compound of claim 21, wherein
$A^{22}$ is Tyr, Phe, or Ala;
$A^{23}$ is Ser, or D-Trp;
$A^{24}$ is Leu, Gly, or Nle;
$A^{25}$ is Arg; and
$A^{26}$ is Ala, or His.

23. A compound of claim 7, wherein
$A^{25}$ is Arg, homo-Arg, diethyl-homo-Arg, or deleted;
$A^{26}$ is Ala, His, 3-Me-His, or 1-Me-His;
$A^{28}$ is Leu, Val, Trp, Nle, Nva, Aib, or Anb;
$A^{29}$ is Asn, Gln, or Trp;
$A^{30}$ is Leu, Ile, Val, Trp, Nle, Nva, Aib, or Anb;
$A^{31}$ is Val, Leu, Ile, Nle, Nva, Aib, or Anb;
$A^{32}$ is Thr, Ser, or D-Trp;
$A^{33}$ is Arg, homo-Arg, or diethyl-homo-Arg;
$A^{34}$ is Gln or Asn;
$A^{35}$ is Arg, homo-Arg, or diethyl-homo-Arg; and
$A^{36}$ is an aromatic amino acid.

24. A compound of claim 23, wherein
$A^{25}$ is Arg, or deleted;
$A^{26}$ is Ala, or His;
$A^{28}$ is Leu, Trp, or Nle;
$A^{29}$ is Asn, or Trp;
$A^{30}$ is Leu, Trp, or Nle;
$A^{31}$ i s Val or Anb;
$A^{32}$ is Thr, or D-Trp;
$A^{33}$ is Arg;
$A^{34}$ is Gln;
$A^{35}$ is Arg; and
$A^{36}$ is Tyr, or Phe.

25. A compound of claim 16, wherein
X is deleted;
$A^{22}$ is an aromatic amino acid, or deleted;
$A^{23}$ is Ser, Thr, D-Trp, or deleted;
$A^{24}$ is Leu, Gly, Ile, Val, Nle, Nva, Aib, Anb, or deleted;
$A^{25}$ is Arg, homo-Arg, diethyl-homo-Arg, or deleted;
$A^{26}$ is Ala, His, 3-Me-His, 1-Me-His, or deleted;
$A^{28}$ is Leu, Val, Trp, Nle, Nva, Aib, or Anb;
$A^{29}$ is Asn, Gln, or Trp;
$A^{30}$ is Leu, Ile, Val, Trp, Nle, Nva, Aib, or Anb;
$A^{31}$ is Val, Leu, Ile, Nle, Nva, Aib, or Anb;
$A^{32}$ is Thr, Ser, or D-Trp;
$A^{33}$ is Arg, homo-Arg, or diethyl-homo-Arg;
$A^{34}$ is Gln, or Asn;
$A^{35}$ is Arg, homo-Arg, or diethyl-homo-Arg; and
$A^{36}$ is an aromatic amino acid.

26. A compound of claim 25, wherein
$A^{22}$ is Tyr, Phe, or deleted;
$A^{23}$ is Ser, D-Trp, or deleted;
$A^{24}$ is Leu, Gly, Nle, or deleted;
$A^{25}$ is Arg, or deleted;
$A^{26}$ is Ala, His, or deleted;
$A^{28}$ is Leu, Trp, or Nle;
$A^{29}$ is Asn, or Trp;
$A^{30}$ is Leu, Trp, or Nle;
$A^{31}$ is Val, or Anb;
$A^{32}$ is Thr, or D-Trp;
$A^{33}$ is Arg;
$A^{34}$ is Gln;
$A^{35}$ is Arg; and
$A^{36}$ is Tyr, or Phe.

27. A compound of claim 26, wherein
$A^{22}$ is Tyr, or Phe;
$A^{23}$ is Ser, or D-Trp;
$A^{24}$ is Leu, Gly, or Nle;
$A^{25}$ is Arg; and
$A^{26}$ is Ala, or His.

28. The compound of claim 2, wherein the —CO—NH— bond between the residues $A^{28}$ and $A^{29}$, $A^{29}$ and $A^{30}$, $A^{30}$ and $A^{31}$, $A^{31}$ and $A^{32}$, $A^{32}$ and $A^{33}$, $A^{33}$ and $A^{34}$, $A^{34}$ and $A^{35}$, or $A^{35}$ and $A^{36}$ is replaced with $CH_2$—NH, $CH_2$—S, $CH_2$—$CH_2$, or $CH_2$—O.

29. The dimeric compound comprising either two peptides of claim 18; two peptides of claim 28; one peptide of claim 1 and one peptide of claim 18; one peptide of claim 2 and one peptide of claim 23; one peptide of claim 3 and one peptide of claim 18; one peptide of claim 1 and one peptide of claim 28; one peptide of claim 2 and one peptide of claim 28; or one peptide of claim 3 and one peptide of claim 28; wherein said dimer is formed by either an amide bond or a disulfide bond between said two peptides.

* * * * *

SEQUENCE LISTING ( 1 ) GENERAL INFORMATION:

( i i i ) NUMBER OF SEQUENCES: 30

( 2 ) INFORMATION FOR SEQ ID NO: 1:

( i ) SEQUENCE CHARACTERISTICS:
        ( A ) LENGTH: 36
        ( B ) TYPE: amino acid
        ( C ) STRANDEDNESS: Not Relevant
        ( D ) TOPOLOGY: linear ( x i ) SEQUENCE DESCRIPTION: SEQ ID NO: 1:

```
Tyr  Pro  Ala  Lys  Pro  Glu  Ala  Pro  Gly  Glu  Asp  Ala  Ser  Pro  Glu  Glu
                         5                        10                       15
Leu  Ser  Arg  Tyr  Tyr  Ala  Ser  Leu  Arg  His  Tyr  Leu  Asn  Leu  Val  Thr
                        20                        25                       30
Arg  Gln  Arg  Tyr                                                                      36
              35
```

( 2 ) INFORMATION FOR SEQ ID NO: 2:

( i ) SEQUENCE CHARACTERISTICS:
        ( A ) LENGTH: 36
        ( B ) TYPE: amino acid
        ( C ) STRANDEDNESS: Not Relevant
        ( D ) TOPOLOGY: linear ( x i ) SEQUENCE DESCRIPTION: SEQ ID NO: 2:

```
Tyr  Pro  Ile  Lys  Pro  Glu  Ala  Pro  Gly  Glu  Asp  Ala  Ser  Pro  Glu  Glu
                         5                        10                       15
Leu  Asn  Arg  Tyr  Tyr  Ala  Ser  Leu  Arg  His  Tyr  Leu  Asn  Leu  Val  Thr
                        20                        25                       30
Arg  Gln  Arg  Tyr                                                                      36
              35
```

( 2 ) INFORMATION FOR SEQ ID NO: 3:

( i ) SEQUENCE CHARACTERISTICS:

(A) LENGTH: 15
(B) TYPE: amino acid
(C) STRANDEDNESS: Not Relevant
(D) TOPOLOGY: linear (ix) FEATURE:
(D) OTHER INFORMATION: Xaa in position 15 is an abbreviation of N—Me—Tyr. The sequence has an acetylated N-terminus (i.e., N—α—Ac), rather than an amino N-terminus (i.e., H$_2$N—). The sequence has an amide C-terminus (i.e., CO—NH$_2$), rather than a carboxyl C-terminus (i.e., CO—OH).

(xi) SEQUENCE DESCRIPTION: SEQ ID NO: 3:

Ala Ser Leu Arg His Phe Leu Asn Leu Val Thr Arg Gln Arg Xaa        15
                 5                   10                  15

(2) INFORMATION FOR SEQ ID NO: 4:

(i) SEQUENCE CHARACTERISTICS:
(A) LENGTH: 15
(B) TYPE: amino acid
(C) STRANDEDNESS: Not Relevant
(D) TOPOLOGY: linear (ix) FEATURE:
(D) OTHER INFORMATION:
The sequence has an amide C-terminus (i.e., CO—NH$_2$), rather than a carboxyl C-terminus (i.e., CO—OH).

(xi) SEQUENCE DESCRIPTION: SEQ ID NO: 4:

Ala Ser Leu Arg His Phe Leu Asn Leu Val Thr Arg Gln Arg Tyr        15
                 5                   10                  15

(2) INFORMATION FOR SEQ ID NO: 5:

(i) SEQUENCE CHARACTERISTICS:
(A) LENGTH: 15
(B) TYPE: amino acid
(C) STRANDEDNESS: Not Relevant
(D) TOPOLOGY: linear (ix) FEATURE:
(D) OTHER INFORMATION: The sequence has an acetylated N-terminus (i.e., N—α—Ac), rather than an amino N-terminus (i.e., H$_2$N—). The sequence has an amide C-terminus (i.e., CO—NH$_2$), rather than a carboxyl C-terminus (i.e., CO—OH).

(xi) SEQUENCE DESCRIPTION: SEQ ID NO: 5:

Ala Ser Leu Arg His Trp Leu Asn Leu Val Thr Arg Gln Arg Tyr        15
                 5                   10                  15

(2) INFORMATION FOR SEQ ID NO: 6:

(i) SEQUENCE CHARACTERISTICS:
(A) LENGTH: 15
(B) TYPE: amino acid
(C) STRANDEDNESS: Not Relevant
(D) TOPOLOGY: linear (ix) FEATURE:
(D) OTHER INFORMATION: Xaa in position 6 is an abbreviation of Thi (2-thienylalanine). The sequence has an acetylated N-terminus (i.e., N—α—Ac), rather than an amino N-terminus (i.e., H$_2$N—). The sequence has an amide C-terminus (i.e., CO—NH$_2$), rather than a carboxyl C-terminus (i.e., CO—OH).

(xi) SEQUENCE DESCRIPTION: SEQ ID NO: 6:

Ala Ser Leu Arg His Xaa Leu Asn Leu Val Thr Arg Gln Arg Tyr        15
                 5                   10                  15

(2) INFORMATION FOR SEQ ID NO: 7:

( i ) SEQUENCE CHARACTERISTICS:
    ( A ) LENGTH: 15
    ( B ) TYPE: amino acid
    ( C ) STRANDEDNESS: Not Relevant
    ( D ) TOPOLOGY: linear ( i x ) FEATURE:
    ( D ) OTHER INFORMATION: The sequence has an acetylated
        N-terminus (i.e., N—α—Ac), rather than an amino N-terminus
        ( i . e . ,   H 2 N — ). The sequence has an amide C-terminus (i.e.,
        CO—NH$_2$), rather than a carboxyl C-terminus (i.e., CO—OH).

( x i ) SEQUENCE DESCRIPTION: SEQ ID NO: 7:

```
Tyr Ser Leu Arg His Phe Leu Asn Leu Val Thr Arg Gln Arg Tyr          15
              5                   10                  15
```

( 2 ) INFORMATION FOR SEQ ID NO: 8:

( i ) SEQUENCE CHARACTERISTICS:
    ( A ) LENGTH: 12
    ( B ) TYPE: amino acid
    ( C ) STRANDEDNESS: Not Relevant
    ( D ) TOPOLOGY: linear ( i x ) FEATURE:
    ( D ) OTHER INFORMATION: The sequence has an acetylated
        N-terminus (i.e., N—α—Ac), rather than an amino N-terminus
        ( i . e . ,   H 2 N — ). The sequence has an amide C-terminus (i.e.,
        CO—NH$_2$), rather than a carboxyl C-terminus (i.e., CO—OH).

( x i ) SEQUENCE DESCRIPTION: SEQ ID NO: 8:

```
Arg His Phe Leu Asn Leu Val Thr Arg Gln Arg Tyr                      12
              5                   10
```

( 2 ) INFORMATION FOR SEQ ID NO: 9:

( i ) SEQUENCE CHARACTERISTICS:
    ( A ) LENGTH: 36
    ( B ) TYPE: amino acid
    ( C ) STRANDEDNESS: Not Relevant
    ( D ) TOPOLOGY: linear ( i x ) FEATURE:
    ( D ) OTHER INFORMATION: Xaa in position 26 is an abbreviation
        of im-DNP—His. The sequence has an acetylated N-terminus
        ( i . e . ,   N — α — A c ), rather than an amino N-terminus (i.e.,
        H$_2$N—). The sequence has an amide C-terminus (i.e.,
        CO—NH$_2$), rather than a carboxyl C-terminus (i.e., CO—OH).

( x i ) SEQUENCE DESCRIPTION: SEQ ID NO: 9:

```
Tyr Pro Ala Lys Pro Glu Ala Pro Gly Glu Asp Ala Ser Pro Glu Glu
              5                   10                  15

Leu Ser Arg Tyr Tyr Ala Ser Leu Arg Xaa Tyr Leu Asn Leu Val Thr
              20                  25                  30

Arg Gln Arg Tyr                                                      36
              35
```

( 2 ) INFORMATION FOR SEQ ID NO: 10:

( i ) SEQUENCE CHARACTERISTICS:
    ( A ) LENGTH: 15
    ( B ) TYPE: amino acid
    ( C ) STRANDEDNESS: Not Relevant
    ( D ) TOPOLOGY: linear ( i x ) FEATURE:
    ( D ) OTHER INFORMATION: The sequence has an amide C-terminus
        ( i . e . ,   C O — N H 2 ), rather than a carboxyl C-terminus (i.e.,
        CO—OH).

( x i ) SEQUENCE DESCRIPTION: SEQ ID NO: 10:

Ala Ser Leu Arg His Tyr Leu Asn Leu Val Thr Arg Gln Arg Tyr       15
                5                   10                  15

(2) INFORMATION FOR SEQ ID NO: 11:

(i) SEQUENCE CHARACTERISTICS:
        (A) LENGTH: 15
        (B) TYPE: amino acid
        (C) STRANDEDNESS: Not Relevant
        (D) TOPOLOGY: linear (ix) FEATURE:
        (D) OTHER INFORMATION: The sequence has an amide C-terminus
            (i.e., $CO-NH_2$), rather than a carboxyl C-terminus (i.e.,
            CO—OH).

(xi) SEQUENCE DESCRIPTION: SEQ ID NO: 11:

Ala Ser Leu Arg His Tyr Leu Asn Leu Val Ala Arg Gln Arg Tyr       15
                5                   10                  15

(2) INFORMATION FOR SEQ ID NO: 12:

(i) SEQUENCE CHARACTERISTICS:
        (A) LENGTH: 15
        (B) TYPE: amino acid
        (C) STRANDEDNESS: Not Relevant
        (D) TOPOLOGY: linear (ix) FEATURE:
        (D) OTHER INFORMATION: The sequence has an amide C-terminus
            (i.e., $CO-NH_2$), rather than a carboxyl C-terminus (i.e.,
            CO—OH).

(xi) SEQUENCE DESCRIPTION: SEQ ID NO: 12:

Ala Ala Leu Arg His Tyr Leu Asn Leu Val Ala Arg Gln Arg Tyr       15
                5                   10                  15

(2) INFORMATION FOR SEQ ID NO: 13:

(i) SEQUENCE CHARACTERISTICS:
        (A) LENGTH: 15
        (B) TYPE: amino acid
        (C) STRANDEDNESS: Not Relevant
        (D) TOPOLOGY: linear (ix) FEATURE:
        (D) OTHER INFORMATION: The sequence has an amide C-terminus
            (i.e., $CO-NH_2$), rather than a carboxyl C-terminus (i.e.,
            CO—OH).

(xi) SEQUENCE DESCRIPTION: SEQ ID NO: 13:

Ala Ser Leu Arg His Tyr Glu Asn Leu Val Thr Arg Gln Arg Tyr       15
                5                   10                  15

(2) INFORMATION FOR SEQ ID NO: 14:

(i) SEQUENCE CHARACTERISTICS:
        (A) LENGTH: 15
        (B) TYPE: amino acid
        (C) STRANDEDNESS: Not Relevant
        (D) TOPOLOGY: linear (ix) FEATURE:
        (D) OTHER INFORMATION: The sequence has an acetylated
           N-terminus (i.e., N—α—Ac), rather than an amino N-terminus
           (i.e., $H_2N-$). The sequence has an amide C-terminus (i.e.,
           CO—$NH_2$), rather than a carboxyl C-terminus (i.e., CO—OH).

(xi) SEQUENCE DESCRIPTION: SEQ ID NO: 14:

Ala Ser Leu Arg His Tyr Leu Asn Leu Val Thr Arg Gln Arg Tyr       15
                5                   10                  15

(2) INFORMATION FOR SEQ ID NO: 15:

(i) SEQUENCE CHARACTERISTICS:
        (A) LENGTH: 15
        (B) TYPE: amino acid
        (C) STRANDEDNESS: Not Relevant
        (D) TOPOLOGY: linear (ix) FEATURE:
        (D) OTHER INFORMATION: Xaa in position 5 is an abbreviation
            of p.Cl.Pro. The sequence has an acetylated N-terminus
            (i.e., N—α—Ac), rather than an amino N-terminus (i.e.,
            $H_2N$—). The sequence has an amide C-terminus (i.e.,
            CO—$NH_2$), rather than a carboxyl C-terminus (i.e., CO—OH).

(xi) SEQUENCE DESCRIPTION: SEQ ID NO: 15:

Ala Ser Leu Arg Xaa Tyr Leu Asn Leu Val Thr Arg Gln Arg Tyr    15
            5                  10              15

(2) INFORMATION FOR SEQ ID NO: 16:

(i) SEQUENCE CHARACTERISTICS:
        (A) LENGTH: 15
        (B) TYPE: amino acid
        (C) STRANDEDNESS: Not Relevant
        (D) TOPOLOGY: linear (ix) FEATURE:
        (D) OTHER INFORMATION: The sequence has an acetylated
            N-terminus (i.e., N—α—Ac), rather than an amino N-terminus
            (i.e., $H_2N$—). The sequence has an amide C-terminus (i.e.,
            CO—$NH_2$), rather than a carboxyl C-terminus (i.e., CO—OH).

(xi) SEQUENCE DESCRIPTION: SEQ ID NO: 16:

Ala Ser Leu Arg His Tyr Glu Asn Leu Val Thr Arg Gln Arg Tyr    15
            5                  10              15

(2) INFORMATION FOR SEQ ID NO: 17:

(i) SEQUENCE CHARACTERISTICS:
        (A) LENGTH: 15
        (B) TYPE: amino acid
        (C) STRANDEDNESS: Not Relevant
        (D) TOPOLOGY: linear (ix) FEATURE:
        (D) OTHER INFORMATION: Xaa in position 15 is an abbreviation
            of N—Me—Tyr. The sequence has an acetylated N-terminus
            (i.e., N—α—Ac), rather than an amino N-terminus (i.e.,
            $H_2N$—). The sequence has an amide C-terminus (i.e.,
            CO—$NH_2$), rather than a carboxyl C-terminus (i.e., CO—OH).

(xi) SEQUENCE DESCRIPTION: SEQ ID NO: 17:

Ala Ser Leu Arg His Tyr Glu Asn Leu Val Thr Arg Gln Arg Xaa    15
            5                  10              15

(2) INFORMATION FOR SEQ ID NO: 18:

(i) SEQUENCE CHARACTERISTICS:
        (A) LENGTH: 15
        (B) TYPE: amino acid
        (C) STRANDEDNESS: Not Relevant
        (D) TOPOLOGY: linear (ix) FEATURE:
        (D) OTHER INFORMATION: The sequence has a myristoylated
            N-terminus (i.e., N—α-myristoyl), rather than an amino
            N-terminus (i.e., $H_2N$—). The sequence has an amide
            C-terminus (i.e., CO—$NH_2$), rather than a carboxyl
            C-terminus (i.e., CO—OH).

(xi) SEQUENCE DESCRIPTION: SEQ ID NO: 18:

Ala Ser Leu Arg His Tyr Leu Asn Leu Val Thr Arg Gln Arg Tyr 15
          5                    10                  15

( 2 ) INFORMATION FOR SEQ ID NO: 19:

( i ) SEQUENCE CHARACTERISTICS:
        ( A ) LENGTH: 15
        ( B ) TYPE: amino acid
        ( C ) STRANDEDNESS: Not Relevant
        ( D ) TOPOLOGY: linear ( i x ) FEATURE:
        ( D ) OTHER INFORMATION: The sequence has a napthaleneacetyl
              N-terminus (i.e., N—α-napthaleneacetyl), rather than an
              amino N-terminus (i.e., $H_2N$—). The sequence has an
              amide C-terminus (i.e., CO—$NH_2$), rather than a carboxyl
              C-terminus (i.e., CO—OH).

( x i ) SEQUENCE DESCRIPTION: SEQ ID NO: 19:

Ala Ser Leu Arg His Tyr Leu Asn Leu Val Thr Arg Gln Arg Tyr 15
          5                    10                  15

( 2 ) INFORMATION FOR SEQ ID NO: 20:

( i ) SEQUENCE CHARACTERISTICS:
        ( A ) LENGTH: 15
        ( B ) TYPE: amino acid
        ( C ) STRANDEDNESS: Not Relevant
        ( D ) TOPOLOGY: linear ( i x ) FEATURE:
        ( D ) OTHER INFORMATION: The sequence has an acetylated
              N-terminus (i.e., N—α—Ac), rather than an amino N-terminus
              ( i . e . , $H_2N$ — ). The sequence has an amide C-terminus (i.e.,
              CO—$NH_2$), rather than a carboxyl C-terminus (i.e., CO—OH).

( x i ) SEQUENCE DESCRIPTION: SEQ ID NO: 20:

Ala Ser Leu Arg His Tyr Leu Asn Leu Val Thr Arg Gln Arg Tyr 15
          5                    10                  15

( 2 ) INFORMATION FOR SEQ ID NO: 21:

( i ) SEQUENCE CHARACTERISTICS:
        ( A ) LENGTH: 15
        ( B ) TYPE: amino acid
        ( C ) STRANDEDNESS: Not Relevant
        ( D ) TOPOLOGY: linear ( i x ) FEATURE:
        ( D ) OTHER INFORMATION: Xaa in position 6 is an abbreviation
              of Bth. The sequence has an acetylated N-terminus (i.e.,
              N—α—Ac), rather than an amino N-terminus (i.e., $H_2N$—).
              The sequence has an amide C-terminus (i.e., CO—$NH_2$),
              rather than a carboxyl C-terminus (i.e., CO—OH).

( x i ) SEQUENCE DESCRIPTION: SEQ ID NO: 21:

Ala Ser Leu Arg His Xaa Leu Asn Leu Val Thr Arg Gln Arg Tyr 15
          5                    10                  15

( 2 ) INFORMATION FOR SEQ ID NO: 22:

( i ) SEQUENCE CHARACTERISTICS:
        ( A ) LENGTH: 15
        ( B ) TYPE: amino acid
        ( C ) STRANDEDNESS: Not Relevant
        ( D ) TOPOLOGY: linear ( i x ) FEATURE:
        ( D ) OTHER INFORMATION: Xaa in position 6 is an abbreviation
              of Bip. The sequence has an acetylated N-terminus (i.e.,
              N—α—Ac), rather than an amino N-terminus (i.e., $H_2N$—).
              The sequence has an amide C-terminus (i.e., CO—$NH_2$), rather than a carboxyl C-terminus (i.e., CO—OH).

( x i ) SEQUENCE DESCRIPTION: SEQ ID NO: 22:

Ala Ser Leu Arg His Xaa Leu Asn Leu Val Thr Arg Gln Arg Tyr       15
                 5                      10                  15

( 2 ) INFORMATION FOR SEQ ID NO: 23:

( i ) SEQUENCE CHARACTERISTICS:
    ( A ) LENGTH: 15
    ( B ) TYPE: amino acid
    ( C ) STRANDEDNESS: Not Relevant
    ( D ) TOPOLOGY: linear ( i x ) FEATURE:
    ( D ) OTHER INFORMATION: Xaa in position 6 is an abbreviation
         of Nal. The sequence has an acetylated N-terminus (i.e.,
         N—α—Ac), rather than an amino N-terminus (i.e., H$_2$N—).
         The sequence has an amide C-terminus (i.e., CO—NH$_2$),
         rather than a carboxyl C-terminus (i.e., CO—OH).

( x i ) SEQUENCE DESCRIPTION: SEQ ID NO: 23:

Ala Ser Leu Arg His Xaa Leu Asn Leu Val Thr Arg Gln Arg Tyr       15
                 5                      10                  15

( 2 ) INFORMATION FOR SEQ ID NO: 24:

( i ) SEQUENCE CHARACTERISTICS:
    ( A ) LENGTH: 36
    ( B ) TYPE: amino acid
    ( C ) STRANDEDNESS: Not Relevant
    ( D ) TOPOLOGY: linear ( i x ) FEATURE:
    ( D ) OTHER INFORMATION: The sequence has an amide C-terminus
         ( i . e . ,   CO — NH2 ), rather than a carboxyl C-terminus (i.e.,
         CO—OH).

( x i ) SEQUENCE DESCRIPTION: SEQ ID NO: 24:

Tyr Pro Ser Lys Pro Asp Asn Pro Gly Glu Asp Ala Pro Ala Glu Asp
                 5                      10                  15

Met Ala Arg Tyr Tyr Ser Ala Leu Arg His Tyr Ile Asn Leu Ile Thr
             20                  25                  30

Arg Gln Arg Tyr                                                    36
         35

( 2 ) INFORMATION FOR SEQ ID NO: 25:

( i ) SEQUENCE CHARACTERISTICS:
    ( A ) LENGTH: 15
    ( B ) TYPE: amino acid
    ( C ) STRANDEDNESS: Not Relevant
    ( D ) TOPOLOGY: linear ( i x ) FEATURE:
    ( D ) OTHER INFORMATION: Xaa in position 6 is an abbreviation
         of Tic. The sequence has an acetylated N-terminus (i.e.,
         N—α—Ac), rather than an amino N-terminus (i.e., H$_2$N—).
         The sequence has an amide C-terminus (i.e., CO—NH$_2$),
         rather than a carboxyl C-terminus (i.e., CO—OH).

( x i ) SEQUENCE DESCRIPTION: SEQ ID NO: 25:

Ala Ser Leu Arg His Xaa Leu Asn Leu Val Thr Arg Gln Arg Tyr       15
                 5                      10                  15

( 2 ) INFORMATION FOR SEQ ID NO: 26:

( i ) SEQUENCE CHARACTERISTICS:
    ( A ) LENGTH: 11
    ( B ) TYPE: amino acid (C) STRANDEDNESS: Not Relevant
            (D) TOPOLOGY: linear (ix) FEATURE:
            (D) OTHER INFORMATION: The sequence has an acetylated
                N-terminus (i.e., N—α—Ac), rather than an amino N-terminus
                (i.e., H2N—). The sequence has an amide C-terminus (i.e.,
                CO—NH₂), rather than a carboxyl C-terminus (i.e., CO—OH).

(xi) SEQUENCE DESCRIPTION: SEQ ID NO: 26:

His Phe Leu Asn Leu Val Thr Arg Gln Arg Tyr                                      11
                 5                      10

(2) INFORMATION FOR SEQ ID NO: 27:

(i) SEQUENCE CHARACTERISTICS:
            (A) LENGTH: 15
            (B) TYPE: amino acid
            (C) STRANDEDNESS: Not Relevant
            (D) TOPOLOGY: linear (ix) FEATURE:
            (D) OTHER INFORMATION: Xaa in position 15 is an abbreviation
                of Thi. The sequence has an acetylated N-terminus (i.e.,
                N—α—Ac), rather than an amino N-terminus (i.e., H₂N—).
                The sequence has an amide C-terminus (i.e., CO—NH₂),
                rather than a carboxyl C-terminus (i.e., CO—OH).

(xi) SEQUENCE DESCRIPTION: SEQ ID NO: 27:

Ala Ser Leu Arg His Phe Leu Asn Leu Val Thr Arg Gln Arg Xaa                      15
                 5                      10                      15

(2) INFORMATION FOR SEQ ID NO: 28:

(i) SEQUENCE CHARACTERISTICS:
            (A) LENGTH: 15
            (B) TYPE: amino acid
            (C) STRANDEDNESS: Not Relevant
            (D) TOPOLOGY: linear (ix) FEATURE:
            (D) OTHER INFORMATION: Xaa in position 5 is an abbreviation
                of Thz. The sequence has an acetylated N-terminus (i.e.,
                N—α—Ac), rather than an amino N-terminus (i.e., H₂N—).
                The sequence has an amide C-terminus (i.e., CO—NH₂),
                rather than a carboxyl C-terminus (i.e., CO—OH).

(xi) SEQUENCE DESCRIPTION: SEQ ID NO: 28:

Ala Ser Leu Arg Xaa Phe Leu Asn Leu Val Thr Arg Gln Arg Tyr                      15
                 5                      10                      15

(2) INFORMATION FOR SEQ ID NO: 29:

(i) SEQUENCE CHARACTERISTICS:
            (A) LENGTH: 15
            (B) TYPE: amino acid
            (C) STRANDEDNESS: Not Relevant
            (D) TOPOLOGY: linear (ix) FEATURE:
            (D) OTHER INFORMATION: Xaa in position 6 is an abbreviation
                of Pcp. The sequence has an acetylated N-terminus (i.e.,
                N—α—Ac), rather than an amino N-terminus (i.e., H₂N—).
                The sequence has an amide C-terminus (i.e., CO—NH₂),
                rather than a carboxyl C-terminus (i.e., CO—OH).

(xi) SEQUENCE DESCRIPTION: SEQ ID NO: 29:

Ala Ser Leu Arg His Xaa Leu Asn Leu Val Thr Arg Gln Arg Tyr                      15
                 5                      10                      15

(2) INFORMATION FOR SEQ ID NO: 30:

(i) SEQUENCE CHARACTERISTICS:
  (A) LENGTH: 15
  (B) TYPE: amino acid
  (C) STRANDEDNESS: Not Relevant
  (D) TOPOLOGY: linear (ix) FEATURE:
  (D) OTHER INFORMATION: The sequence has an acetylated
    N-terminus (i.e., N—α—Ac), rather than an amino N-terminus
    (i.e., H 2 N — ). The sequence has an amide C-terminus (i.e.,
    CO—NH$_2$), rather than a carboxyl C-terminus (i.e., CO—OH).

(xi) SEQUENCE DESCRIPTION: SEQ ID NO: 30:

Phe Ser Leu Arg His Phe Leu Asn Leu Val Thr Arg Gln Arg Tyr
          5                   10                  15